US008632570B2

(12) United States Patent
Biedermann et al.

(10) Patent No.: US 8,632,570 B2
(45) Date of Patent: Jan. 21, 2014

(54) STABILIZATION DEVICE FOR BONES COMPRISING A SPRING ELEMENT AND MANUFACTURING METHOD FOR SAID SPRING ELEMENT

(75) Inventors: Lutz Biedermann, VS-Villingen (DE); Wilfried Matthis, Weisweil (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1499 days.

(21) Appl. No.: 10/982,188

(22) Filed: Nov. 5, 2004

(65) Prior Publication Data
US 2005/0154390 A1 Jul. 14, 2005

Related U.S. Application Data

(63) Continuation-in-part of application No. 10/966,921, filed on Oct. 15, 2004.

(60) Provisional application No. 60/518,469, filed on Nov. 7, 2003, provisional application No. 60/523,946, filed on Nov. 21, 2003, provisional application No. 60/550,182, filed on Mar. 3, 2004.

(30) Foreign Application Priority Data
Nov. 7, 2003 (DE) .................................. 103 51 978

(51) Int. Cl.
*A61B 17/70* (2006.01)
(52) U.S. Cl.
USPC ...................................................... 606/246
(58) Field of Classification Search
USPC ........... 606/60, 246, 250, 254, 255, 257, 259, 606/261, 264–267, 275, 279, 301, 304, 308, 606/314; 623/17.13; 403/397; 411/6, 392, 411/544
See application file for complete search history.

(56) References Cited

U.S. PATENT DOCUMENTS

| 4,273,116 A | 6/1981 | Chiquet |
| 4,959,064 A | 9/1990 | Engelhardt |

(Continued)

FOREIGN PATENT DOCUMENTS

| DE | 29 25 085 | 6/1979 |
| DE | 299 15 204 UI | 8/1999 |

(Continued)

OTHER PUBLICATIONS

International Search Report dated Feb. 24, 2005 for Application No. PCT/EP2004/012592.

(Continued)

*Primary Examiner* — Pedro Philogene
*Assistant Examiner* — David Comstock
(74) *Attorney, Agent, or Firm* — Christie, Parker & Hale, LLP

(57) ABSTRACT

An elastic or flexible element for use in a stabilization device for bones or vertebrae is provided. The elastic or flexible element is provided in the form of an essentially cylindrical body with a first end and a second end opposite thereto, wherein at least one of the opposite ends of the cylindrical body comprises a coaxial bore hole with an internal thread for connecting to a shaft and/or a head of a bone screw or for connecting to a rod section. The present invention further provides a bone anchoring element, e.g. a bone screw, with a shaft for the anchoring in a bone, whereby the shaft comprises an elastic or flexible section which is formed integrally with the shaft or as a separate elastic or flexible element. It is preferable for the elastic section to be implemented in the form of a helical spring. Moreover, the present invention provides a stabilization device for bones, for instance for vertebrae, said device comprising at least one bone anchoring element according to the invention, a second bone anchoring element and a rod or plate connecting the bone anchoring elements.

19 Claims, 16 Drawing Sheets

(56) References Cited

U.S. PATENT DOCUMENTS

| | | |
|---|---|---|
| 5,074,865 A | 12/1991 | Fahmy |
| 5,306,310 A | 4/1994 | Siebels |
| 5,320,644 A | 6/1994 | Baumgartner |
| 5,423,816 A | 6/1995 | Lin |
| 5,423,817 A | 6/1995 | Lin |
| 5,474,555 A | 12/1995 | Puno et al. |
| 5,486,174 A | 1/1996 | Fournet-Fayard et al. |
| 5,672,175 A | 9/1997 | Martin |
| 6,162,223 A | 12/2000 | Orsak et al. |
| 6,267,764 B1 | 7/2001 | Elberg |
| 6,402,750 B1 | 6/2002 | Atkinson et al. |
| 6,770,094 B2 | 8/2004 | Fehling et al. |
| 7,621,912 B2 | 11/2009 | Harms et al. |
| 2001/0008704 A1 | 7/2001 | Harder et al. |
| 2002/0035366 A1 | 3/2002 | Walder et al. |
| 2002/0055737 A1 | 5/2002 | Lieberman |
| 2002/0055740 A1 | 5/2002 | Lieberman |
| 2002/0055742 A1 | 5/2002 | Lieberman |
| 2002/0198527 A1 | 12/2002 | Muckter |
| 2003/0009223 A1 | 1/2003 | Fehling et al. |
| 2003/0055427 A1 | 3/2003 | Graf |
| 2003/0100904 A1 | 5/2003 | Biedermann |
| 2003/0109880 A1 | 6/2003 | Shirado et al. |
| 2003/0171749 A1 | 9/2003 | Le Couedic et al. |
| 2003/0191470 A1 | 10/2003 | Ritland |
| 2003/0220643 A1 | 11/2003 | Ferree |
| 2004/0049189 A1 | 3/2004 | Le Couedic et al. |
| 2004/0267260 A1 | 12/2004 | Mack et al. |
| 2005/0055025 A1 | 3/2005 | Zacouto et al. |
| 2005/0056979 A1 | 3/2005 | Studer et al. |
| 2005/0085815 A1 | 4/2005 | Harms et al. |
| 2007/0049937 A1 | 3/2007 | Matthis et al. |
| 2007/0198088 A1 | 8/2007 | Biedermann et al. |

FOREIGN PATENT DOCUMENTS

| | | |
|---|---|---|
| DE | 299 15 204 U1 | 1/2000 |
| EP | 0 529 275 A2 | 3/1993 |
| EP | 0 669 109 B1 | 2/1994 |
| EP | 0 677 277 A2 | 3/1995 |
| EP | 0 820 731 A2 | 1/1998 |
| EP | 0 950 389 A2 | 10/1999 |
| EP | 1 188 416 A1 | 3/2002 |
| EP | 1 273 269 A2 | 4/2002 |
| EP | 1 273 276 A2 | 1/2003 |
| EP | 1273276 | 1/2003 |
| EP | 1 488 751 A1 | 12/2004 |
| FR | 2 634 371 | 1/1990 |
| FR | 2 702 361 | 9/1994 |
| FR | 2 717 370 | 9/1995 |
| FR | 2 718 946 | 10/1995 |
| GB | 2 382 304 A | 5/2003 |
| JP | 61-90816 | 5/1986 |
| JP | 10-122285 | 5/1998 |
| JP | 11-076261 A | 3/1999 |
| JP | 2002-172119 | 6/2002 |
| JP | 2003-10199 | 1/2003 |
| JP | 2003-180707 | 7/2003 |
| KR | 2003-0013282 A | 2/2003 |
| WO | WO 95/19153 | 7/1995 |
| WO | WO 96/15729 | 5/1996 |
| WO | WO 96/16608 | 6/1996 |
| WO | WO 97/07744 | 3/1997 |
| WO | WO 99/65425 | 12/1999 |
| WO | WO 02/07621 A1 | 1/2002 |
| WO | WO 02/07622 A1 | 1/2002 |
| WO | WO 02/24087 A1 | 3/2002 |
| WO | WO 03/047442 A1 | 6/2003 |
| WO | WO 2004/105577 A2 | 12/2004 |

OTHER PUBLICATIONS

European Search Report dated Apr. 1, 2005 for Application No. PCT/EP2004/012591.

International Search Report dated Mar. 11, 2005 for Application No. PCT/EP2004/011782.

International Search Report dated Apr. 29, 2005 for Application No. PCT/EP2004/011782.

Abstract of FR 2634371, Flegeau Gerard. "Hip prosthesis and method for manufacturing such a prosthesis" Published Jan. 26, 1990, 1 page.

Abstract of EP 0669109, Sulzer Medizinal Technik AG. "Stabilizer for adjacent vertebrae" Published Aug. 30, 1995, 1 page.

Abstract of EP 0950389, Aesculap AG & Co KG. "Intervertebral fusion implant" Published Oct. 20, 1999, 1 page.

Patent Abstracts of Japan for Publication No. 2002-172119, Published Jun. 18, 2002, in the name of Yoshinori.

Extended European Search Report dated Feb. 24, 2009 for EP 08 00 3789, 6 pages.

Translation of the European Search Opinion for EP 08 00 3789, 5 pages.

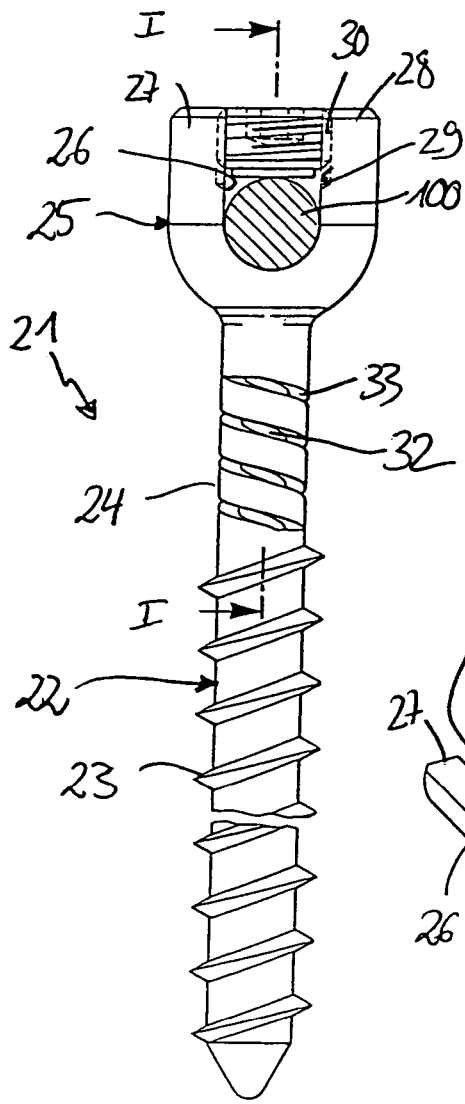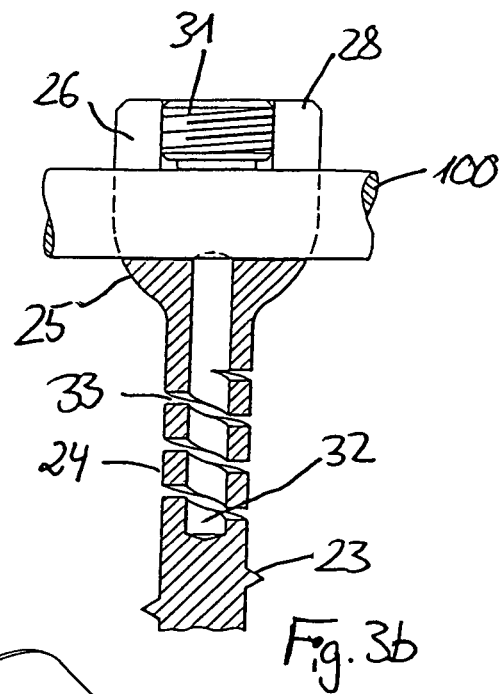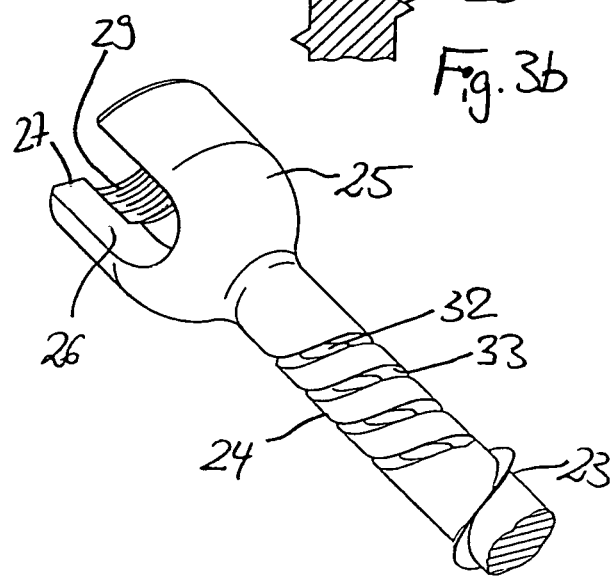
Fig. 3a
Fig. 3b
Fig. 3c

STABILIZATION DEVICE FOR BONES COMPRISING A SPRING ELEMENT AND MANUFACTURING METHOD FOR SAID SPRING ELEMENT

CROSS REFERENCE TO RELATED APPLICATIONS

This application is a continuation-in-part of U.S. patent application Ser. No. 10/966,921 filed Oct. 15, 2004. This application claims the benefit of priority, and incorporates by reference in their entirety, from U.S. patent application Ser. No. 10/966,921 filed Oct. 15, 2004, from U.S. Provisional Application Ser. No. 60/518,469 filed Nov. 7, 2003, from U.S. Provisional Application Ser. No. 60/523,946 filed Nov. 21, 2003, and from U.S. Provisional Application Ser. No. 60/550,182 filed Mar. 3, 2004. This application claims the benefit of foreign priority under 35 U.S.C. §119(a)-(d), and incorporates by reference in its entirety, from German Patent Application No. 103 51 978.5 filed Nov. 7, 2003 in Germany.

FIELD OF THE INVENTION

The present invention relates to a stabilization device for bones comprising a plurality of bone anchoring elements and a connector connecting the bone anchoring elements, the stabilization device being particularly useful for application in spinal surgery or trauma surgery. At least one bone anchoring element comprises a flexible rod-shaped element and a manufacturing method for bone anchoring elements of this type.

BACKGROUND OF THE INVENTION

Fixation and stabilization devices are known for the fixation of bone fractures or for the stabilization of the spinal column, which consist of at least two bone screws that are anchored in the bone or the vertebra and/or are connected via a plate or a rod. Such rigid systems do not permit any movement of the bone parts or vertebrae because they are fixed relative to each other.

For example, U.S. Pat. No. 5,474,555 describes an apparatus for internal fixation of the spine, with a screw element and a receiving part for connection to a rod, in which the screw element to be anchored in the bone is connected to the receiving part such that swiveling motions of the screw element and the receiving part are possible. However, the described solution does not allow for the mutual stabilization of bone parts and controlled partial motion.

However, for certain indications, a dynamic stabilization is desirable, in which the bone parts and vertebrae to be stabilized are able to carry out a controlled limited movement relative to each other. One option for realizing the dynamic stabilization device is the use of an elastic element instead of a rigid rod to connect the bone anchoring elements.

U.S. 2003/0109880 A1 describes a dynamic stabilization device for vertebrae is known, which comprises a first and a second screw to be anchored in the vertebra, each of which has a receiving part for the insertion of a spring connecting the screws, and a spring of this type. The spring itself, as a whole, is provided in the form of a coil spring with closely neighboring turns, similar to a tension spring and is fixed in the receiving parts by means of clamping screws. This, however, poses the risk that the spring, owing to its flexibility, evades the pressure of the clamping screw, thus causing the fixation between the bone screw and the spring to loosen. A further disadvantage of the device is that the elasticity of the spring, with otherwise identical spring characteristics, depends on the length of the spring.

EP 0 669 109 B1 discloses a stabilization device for stabilizing neighboring vertebrae, which comprises two monoaxial pedicle screws and a strap that is fixed in the receiving parts of the pedicle screws by means of a clamping screw, and which contains a pressure-resistant support element that is mounted on the strap. However, a stabilization device of this type fails to provide for stabilization against torsion. As in the stabilization device described above, the elasticity of the connection of the two bone anchoring elements, with otherwise identical characteristics of the spring elements, depends on the length of the spring coils and/or the spacing of the bone anchoring elements.

A joint fixation device, for example, for a wrist or a knee joint, is disclosed in U.S. Pat. No. 6,162,223. The apparatus comprises a fixation rod that is connected to bone anchoring elements at its ends and consists of two parts, wherein the two parts of the fixation rod are connected to one another via a flexible coupling and wherein the fixation rods and the coupling are arranged outside of the body. The two pieces of the fixation rod are not firmly connected to the coupling part, but rather can move freely along a bore hole in the coupling part. The ends of the two parts of the fixation rod that are facing each other are designed hemispherically and abut against each other, thus simulating a type of joint whose freedom of movement is limited by the flexible coupling. Owing to the type of connection to the two-piece fixation rod, the diameter of the coupling part is always larger than the diameter of the fixation rod. Owing to its complex and voluminous structure, this known joint fixation apparatus is not suitable for internal use on the spinal column or other bones.

U.S. 2003/0220643 A1 discloses a strechable element to be used in an apparatus for preventing full extension between upper and lower vertebral bodies.

U.S. Pat. No. 4,959,064 discloses a dynamic bone fixation screw for rejoining fracture fragments of a bone to their approximate original mutual dispositions. The screw includes a threaded distal end member for threaded engagement with one of the bone fragments and a head member at a proximal end for engagement with another of the bone fragments. A spring member is integral with and connects the threaded distal member with the head member. Alternative designs for dynamic bone fixation screws with a flexible shaft to stabilize a joint or a bone fracture are disclosed by EP 1 273 269 A2. However, none of these screws are connected with each other via a connecting member.

Therefore, there remains a need for bone stabilization devices that permit limited movement of vertebrae or bones that are to be connected to each other.

SUMMARY OF THE INVENTION

The present invention provides a bone stabilization device comprising a plurality of bone anchoring elements and a connecting element connecting at least two bone anchoring elements, wherein at least one of the bone anchoring elements comprises an essentially cylindrical body having at one end a threaded portion for anchoring into bone tissue and further comprising a length of a flexible section having a helical slotted opening in the outer surface of the cylindrical body, the slot extending radially inward.

The flexible section can be a spring-like element that is simple and compact in design, easy to handle while providing high operational safety, and which can be combined with other elements in as many ways as possible to form a dynamic stabilization device for vertebrae or bones that are to be connected. Also provided is a manufacturing method for the flexible element.

In certain preferred embodiments of the invention, the bone anchoring element comprises an integral cylindrical body and a head. In certain other preferred embodiments of the invention, the flexible section is a separate component having opposing ends to which the threaded portion and head can be connected to form the bone anchoring element.

In certain preferred embodiments of the invention, the flexible section further comprises one or more of the following:
- a coaxial longitudinal bore extending throughout the section;
- the flexible section has two opposite ends, the first length of rigid section being adjacent a first end and a second length of rigid section being adjacent the opposite second end;
- the flexible section has a first diameter and the rigid section has a second diameter different at least at one point from the first diameter;
- the flexible section has two symmetrical concave surfaces in the outer surface, the concavity being an arcuate shape the arc of which extends along the longitudinal axis;
- the flexible section has an outer diameter that varies along a length of the flexible section;
- the flexible section further comprising a core;
- the flexible section comprises a first material and the core comprises a second material;
- the core has at least in a part of the flexible section a cross section with an anisotropic shape; and
- the core is accommodated in the bore with a tolerance in direction of the longitudinal axis.

In certain embodiments where the flexible section is a separate component of the bone anchoring element, the flexible section further comprises one or more of the following:
- an internal thread is provided at each of the two ends;
- an essentially cylindrical body with a first end and a second end opposite thereto, with the first end of said body comprising a cylindrical projection with an external thread for connecting to a shaft or to a head of a bone screw, for connecting to a rod section or for connecting to a plate;
- the second end of which comprises a cylindrical projection with an external thread for connecting to a shaft or to a head of a bone screw, for connecting to a rod section or for connecting to a plate;
- a coaxial bore hole adjacent to its second end;
- at least in a section of the coaxial bore hole that is adjacent to the second end, an internal thread for connecting to a shaft or to a head of a bone screw, for connecting to a rod section or for connecting to a plate;
- the bore hole extends over the entire length;
- the body is tubular in shape with a continuous coaxial bore hole and a recess in the wall that extends in the form of a helix in the direction of the cylinder axis, wherein, in radial direction, the recess ends in the bore hole;
- a core is provided in the bore hole;
- the flexible section is provided as a helical spring-like structure; and
- the flexible section is made from a body-compatible material, in particular titanium.

In certain preferred embodiments of the invention, the connecting element comprises a plate having through holes in which a head of a bone anchoring element is received. Alternatively, the plate can have a cylindrical projection with an external thread for connecting with the bone anchoring element having a cooperating internal thread at one end.

In certain other preferred embodiments of the invention, the connecting element comprises a rod-shaped element that is received in a U-shaped opening in the head of two or more bone anchoring elements.

The invention also provides a method for making the flexible section for the bone anchoring element. The method comprises: providing a body that is cylindrical in shape, and forming a helix-shaped recess by removing material, from the outer surface by metal-cutting along a helix that extends coaxial to the main axis of the cylindrical body. In certain preferred embodiments, the cylindrical body includes an integral head element.

In certain embodiments of the invention, the method further comprises forming a bore hole along the main axis of the cylindrical body. In addition, when the flexible section is a separate component of the bone anchoring element, the method further comprises forming an internal thread in one of the two end sections of the bore hole.

In certain embodiments of the invention, the method for making the flexible section includes one or more of the following steps:
- forming the bore hole such that the helix-shaped recess in the outside wall of the cylindrical body formed by metal-cutting ends in the bore hole in radial direction;
- forming an internal thread in the other end section of the bore hole;
- forming one cylindrical projection with an external thread on each of the two ends of the cylindrical body by means of metal-cutting turning;
- forming a helix-shaped recess by removing material, from outside, by metal-cutting along a helix that extends coaxial to the main axis of the cylindrical body and forming a bore hole along the main axis of the cylindrical body;
- finishing, by means of milling, the runout of the helix-shaped recess after forming the bore hole in order to remove a sharp edge on the inside of the bore hole, and deburring the flexible section thus formed;
- forming a bore hole coaxial to the main axis of the cylindrical body with said bore hole being adjacent at least to the first end of the cylindrical body;
- cutting by means of wire-EDM, laser treatment or water jet treatment of a recess along a helix extending coaxial to the main axis of the cylindrical body;
- either forming, by means of metal-cutting turning, a cylindrical projection with a diameter that is smaller than the predetermined external diameter of the cylindrical body provided in step (a), and forming an external thread on the surface of the cylindrical projection at the first end of the cylindrical body, or forming an internal thread in the bore hole formed in step (b) in a section adjacent to the first end of the cylindrical body;
- forming the bore hole from the first to the second end of the cylindrical body;
- forming an internal thread in the bore hole in a section adjacent to the second end of the cylindrical body;
- forming, by means of metal-cutting turning, a second cylindrical projection with a diameter that is smaller than the predetermined external diameter of the cylindrical body, and forming an external thread on the surface of the second cylindrical projection at the second end of the cylindrical body; and
- providing two runouts of the helix-shaped recess in the form of a quarter circle.

The invention provides the advantage that a flexible element or a flexible section can, optionally, be combined with rigid rod-shaped elements of various lengths to form a flexible bone anchoring element with various shafts and/or heads thereby forming a bone screw with flexible properties. Depending on the flexible element used, the bone screw then has predetermined elastic properties, such as a certain capability of compression and extension in axial direction as well as a certain flexural strength and torsional stiffness.

In particular, the flexible element can be connected to rod-shaped components which vary in thickness or with plates of various shapes and lengths for use in spinal surgery and/or trauma surgery.

The invention is advantageous in that its elastic section allows the bone anchoring element to receive axial forces acting in the direction of the bone anchoring element's shaft axis, as well as flexural forces and torsional forces. This allows for the motion of the bone part or vertebra in which the bone anchoring element is anchored with the motion being limited by the retroactive force. The elastic properties of the of the flexible section of the bone anchoring element are easy to implement during the production of the bone anchoring element by changing the dimensions of the flexible section. The bone anchoring element can be connected to the known connecting elements, such as plates and rods. Thus, it is possible to provide a dynamic stabilization device with a desired limitation of motion by selecting bone anchoring elements with suitable elastic properties and using these in combination with conventional plates or rods.

The invention also provides methods for stabilization of bones or vertebrae using the stabilization devices described herein. Thus, in a patient in need of bone or vertebrae stabilization, at least two bone anchoring elements are inserted into bone on opposite sides of a fracture, or break, or other instability, or on two adjacent vertebrae. At least one of the bone anchoring elements comprises a bone anchoring section to be anchored in the bone and flexible section as described herein. The connecting element used to connect the bone anchoring elements thereby providing stabilization with a predetermined limited movement.

Additional features and characteristics of the invention are evident from the description of embodiments on the basis of the attached drawings.

BRIEF DESCRIPTION OF THE DRAWINGS

FIG. 3a shows an elevational view of a bone anchoring element according to another embodiment in accord with the present invention, with a rod (shown in section) inserted;

FIG. 3b shows a partial sectional view of the bone anchoring element along line I-I in FIG. 3a;

FIG. 3c shows a partial perspective view of the bone anchoring element shown in FIG. 3a, with no rod inserted;

FIG. 4 is used;

FIG. 7a shows an elevational view of a bone anchoring element in accord with a further alternative embodiment in accord with the present invention;

FIG. 7b shows a sectional view of the bone anchoring element of FIG. 7a;

FIG. 9a shows a lateral view of a first embodiment of a flexible section as a separate element in accord with one embodiment of the present invention;

FIG. 9b shows a sectional view of the element of FIG. 9a;

FIG. 10b shows a modification of the application FIG. 10a;

FIG. 14a shows a lateral view of another alternative embodiment of a flexible section as a separate element in accord with certain aspects the present invention;

FIG. 14b shows a lateral view, turned by 90 degrees, of the element of FIG. 14a;

FIG. 20b shows a sectional view of a bone anchoring element used in the stabilization device of FIG. 20a;

DETAILED DESCRIPTION OF THE INVENTION

The invention and various embodiments thereof are presented in FIGS. 1 through 22 and the accompanying descriptions wherein like numbered items are identical. As used herein, the terms flexible element, flexible section, spring like element, elastic element or elastic section refer to an element or section of an element that can have spring-like elastic or flexible properties.

Bone stabilization devices in accord with the present invention can be designed and implemented in a wide variety of ways. Typically, they will comprise two or more bone anchoring elements and a connecting element connecting at least two bone anchoring elements. At least one of the bone anchoring elements comprises an essentially cylindrical body segment having at one end a threaded portion for anchoring into bone tissue and further comprising a length of a flexible section having a helical slotted opening (or recess) in the outer surface of the cylindrical body, the slot extending radially inward. In certain preferred embodiments, a plurality of flexible sections can be used to provide the desired limited movement of the stabilized bones or vertebrae. In addition to locating the flexible section in a bone anchoring element, a flexible section also can be located in a connecting element, particularly in a rod-shaped connecting element.

Figure 1:
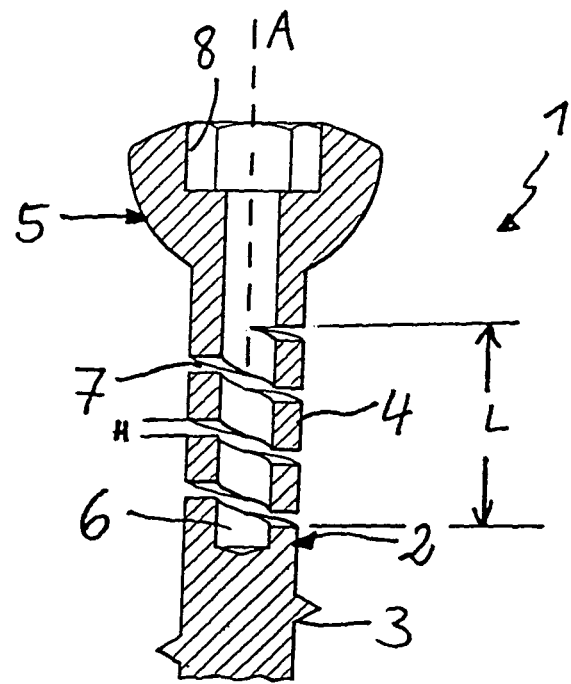
FIG. 1 shows a elevational, partial, sectional view of one embodiment of a bone anchoring element in accord with the present invention.
Figure 2:
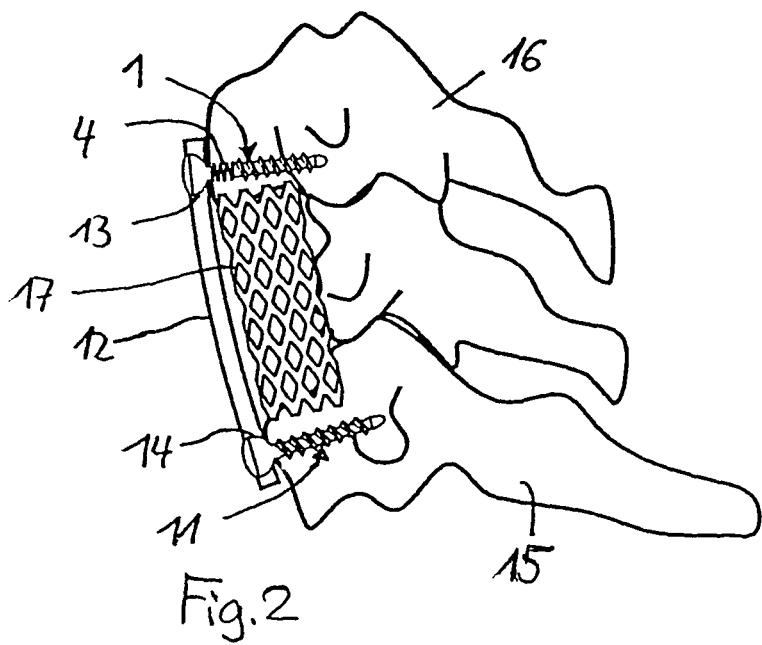
FIG. 2 shows a schematic representation of a stabilization device according to one embodiment of the present invention, wherein said stabilization device comprises the bone anchoring element according to FIG. 1.

Bone anchoring elements useful in the practice of the present invention can have a variety of structures. As is illustrated in FIGS. 1 and 2, the one embodiment of a bone anchoring element 1 is implemented in the form of a single-piece bone screw comprising shaft 2 with a first threaded section 3, which is to be anchored in the bone, having a bone screw thread. The bone anchoring element 1 also has a second section 4, which is adjacent to first section 3 and bears no bone screw thread, as well as head 5 adjacent to the second section. From the free end of head 5, a pocket bore 6 with a predetermined diameter extends throughout head 5 and the second section 4 in a direction coaxial to screw axis A. In the second section 4, shaft 2 comprises recess 7 in the surface, which extends along the surface in the form of a helix in the direction of axis A) having a pre-determined slope and a pre-determined length. In this embodiment, the recess 7 extends from the surface in the radial direction to the bore 6. Thus, second section 4 is implemented to be flexible in the form of a helical spring-like structure. The length L of the flexible section in the direction of the screw axis, the height H of recess 7 in the direction of the screw axis, the slope of the spiral, and the diameter of coaxial bore 6 are selected such that the helical spring is provided with the desired stiffness in response to the action of axial forces, flexural forces, and torsional forces on the bone screw. Alternatively, as another variable, the depth of the recess radially inward can be varied such that is does not extend fully to the bore to vary flexibility or stiffness. Spiral and helical as used herein is intended to cover a helix-type shape.

In the embodiment shown, head 5 is implemented to have a lenticular shape and further comprises hexagonal recess 8 for a hexagon socket screw key at its free end. However, different head shapes and/or a different recess, such as a recessed head, for engagement of a screw-in tool also can be used, as is well known to those skilled in the art.

As shown in FIG. 2, one embodiment of a stabilization device according to the present invention consists of a first bone anchoring element 1 in the form of the bone screw of FIG. 1 and a second bone anchoring element 11, which can be used as a conventional bone screw with no flexible section, as well as a plate 12 with recesses 12, 13 through which the shaft of the bone screws can be guided and the bone screw head received.

In the embodiment shown in FIG. 2, the stabilization device is designed to stabilize two vertebrae 15, 16 which are connected rigidly to each other by means of a fusion element 17, e.g., a titanium cylindrical element, following the removal of the intervertebral disc or after removal of an intervening vertebra.

In operation, the shafts of bone screws 1, 11 are first guided through recesses 12, 13 of the plate and then screwed into the respective vertebra 15, 16 until plate 12 rests against the vertebra. In this arrangement, the flexible section 4 of bone screw 1 can reside inside the vertebra. In this case, the vertebra can perform a limited motion only along the direction of the screw axis. When the in-growth of the fusion element results in said element being lowered into the bone the bone screw yields to some extent because of its flexible section. This prevents the generation of undesirable tension.

The stabilization device as described can also utilize two bone screws, each with a flexible section 4. Further, to accommodate more than two screws the plate can be modified to provide the corresponding number of recesses for receiving the bone screws. The stabilization device is not only suitable for use at the spinal column but can also be applied in other cases in which osteosynthesis using plates is performed.

Another embodiment of a bone anchoring element 21 useful in the practice of the present invention, as shown in FIGS. 3a to 3c, is implemented in the form of a monoaxial bone screw for connecting to a rod 100. The monoaxial bone screw comprises a shaft 22 with a first section 23 which is to be anchored in the bone and bears a bone screw thread and a section 24, which is adjacent to first section 23 and bears no bone screw thread, as well as a receiving part 25 for the reception of rod 100, whereby said receiving part 25 and shaft 21 are connected as a single (integral) part. The receiving part 25 can be essentially cylindrical in shape and includes a recess 26 which initiates at its free end and has a cross-section of a size just large enough for rod 100 to be inserted and fit in the base of recess 26. Any cross section can be used provided that the rod can be placed into the receiving part. Preferably a U-shaped cross section is used. U-shaped recess 26 forms two free legs 27, 28, which bear an internal screw thread 29 adjacent to their free end, whereby said internal screw thread 29 engages a corresponding external screw thread 30 of internal screw 31 that is to be screwed in between the legs for fixing rod 100.

As is particularly apparent from FIG. 3b, a coaxial bore 32 with a pre-determined depth extends from the base of U-shaped recess 26 towards bone screw thread section 23 through section 24 which bears no bone screw thread. The second section 24 of the shaft comprises a recess 33 which extends spirally along the surface of the shaft like a helix in the direction of the screw axis and extends in radial direction into bore 32. This provides for the flexibility of second section 24 and acts as a helical spring-like structure. In the example shown, the helix extends along the axis having a rotation counter to the bone thread, particularly when the recess extends radially into the bore.

Another embodiment of a stabilization device according to the present invention consists of at least one bone anchoring element implemented in the form of a monoaxial screw with an flexible section 24, a second bone anchoring element implemented as a conventional monoaxial or polyaxial bone screw with no elastic section and a connecting rod. Instead of using a conventional monoaxial or polyaxial bone screw as a second anchoring element, the stabilization device may comprise a monoaxial bone screw according to FIGS. 3a-3c as the second anchoring element.

In operation, the bone anchoring elements are screwed into their respective bone or, in applications on the spinal column into the respective vertebrae, followed by the insertion of rod 100 in the receiving parts, and fixation of the rod by means of the internal screw. In the process, monoaxial bone screw 21 is screwed into bone tissue so that the flexible section 24 protrudes preferably at least partially beyond the surface of the bone or vertebra. If the bone or vertebra is moved from its resting position, which is to be stabilized, flexible section 24 exerts a retroactive force on the bone or vertebra, which returns it to the resting position and thus limits its motion.

Alternatively, the bone screw can be screwed far enough for elastic section 24 to protrude not at all or only very little beyond the surface of the bone. In this case the spring action of the flexible section can provide for some yield after adjustment.

Figure 4:
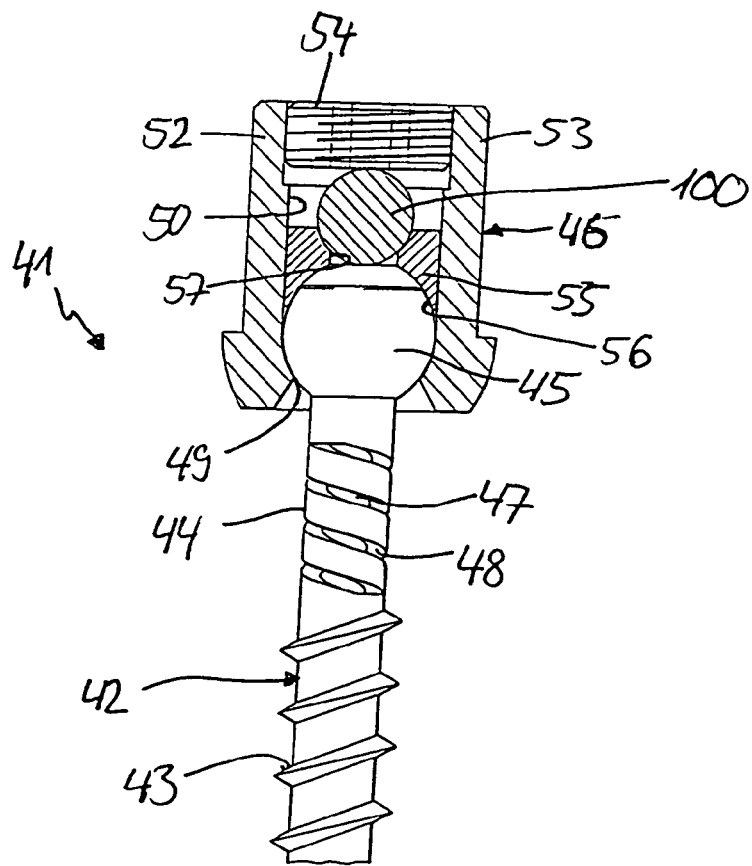
FIG. 4 shows a partial view, partially in section, of another embodiment of a bone anchoring element in accord with the present invention.

An alternative embodiment of a bone anchoring element useful in the present invention is shown in FIG. 4. The bone anchoring element 41 is implemented in the form of a polyaxial bone screw. This screw comprises a single-piece screw element with a shaft 42 with a first section 43 which is to be anchored in the bone and a second section 44 which is adjacent to first section 43 and bears no bone screw thread, as well as a shead 45 which can have a spherically shaped segment, that is adjacent to second section 44. Head 45 is held by a receiving part 46. As in the preceding embodiments, second section 44, a flexible section, is implemented in the form of a helical recess in the surface of shaft 42, which comprises a coaxial bore 47, which extends from the free end of the head through the second section, and recess 48 extends radially in the wall to the bore.

The receiving part 46 can have any shape. In the embodiment shown, the receiving part 46 is implemented in a conventional manner to be essentially cylindrical in shape and comprises at one of its ends a bore 49 in an axially symmetrical alignment with a diameter that is larger than that of shaft 42 and smaller than that of head 45. Moreover, receiving part 46 comprises a coaxial second bore 50 which is open at the end opposite to first bore 49 and whose diameter is sufficiently large for the screw element to be guided through the open end with the shaft through the first bore 49 until head 45 rests on the edge of first bore 49. Like receiving part 25 of the previous embodiment, receiving part 46 comprises a U-shaped recess which initiates at its free end, extends in the direction of first bore 49 and forms two free legs 52, 53. In an area adjacent to their free ends, legs 52, 53 comprise an internal screw thread which engages a corresponding external screw thread of an internal screw 54 for fixing rod 100 in the receiving part and also thereby fixing the bone screw head and the angle of the shaft of the bone screw.

Moreover, a pressure element 55 is provided for the fixation of the screw head in the receiving part, said pressure element being implemented such that it comprises at it side facing head 45 a spherical recess 56 whose radius is essentially identical to the radius of the spherical segment-shaped section of head 45. The outer diameter of pressure element 55 is selected such that the pressure element is displaceable within receiving part 46 in the direction towards head 45. Moreover, the pressure element comprises a coaxial bore 57 allowing a screw-in tool to engage a recess in screw head 45 (not shown herein) for driving the screw into bone tissue. Any other shaped pressure element can be used provided that the pressure element fixes the screw head in the receiving part.

Another embodiment of a stabilization device according to the present invention comprises at least two bone anchoring elements and a rod, whereby at least one of the bone anchoring elements is implemented as a polyaxial bone screw with a shaft with an flexible section 44, as illustrated in FIG. 4. The second bone anchoring element can be implemented as a conventional monoaxial or polyaxial bone screw without a flexible section or it can be implemented as a monoaxial bone screw or as a polyaxial bone screw with a flexible section as described herein.

In operation, the screw element is first inserted into the receiving part until head 45 rests next to the edge of first bore 49. Then, the screw element is screwed into the bone or vertebra such that flexible section 44 protrudes preferably at least partially beyond the surface of the bone. Subsequently, the rod is inserted, the angular arrangement of the receiving part in relation to the screw element is adjusted and then fixed by tightening the internal screw. Similar to the preceding embodiment, the flexible section permits some limited motion around the resting position.

Alternatively, the shaft may be screwed in sufficiently for the flexible section to protrude not at all or only very little beyond the surface of the bone.

Figure 5:
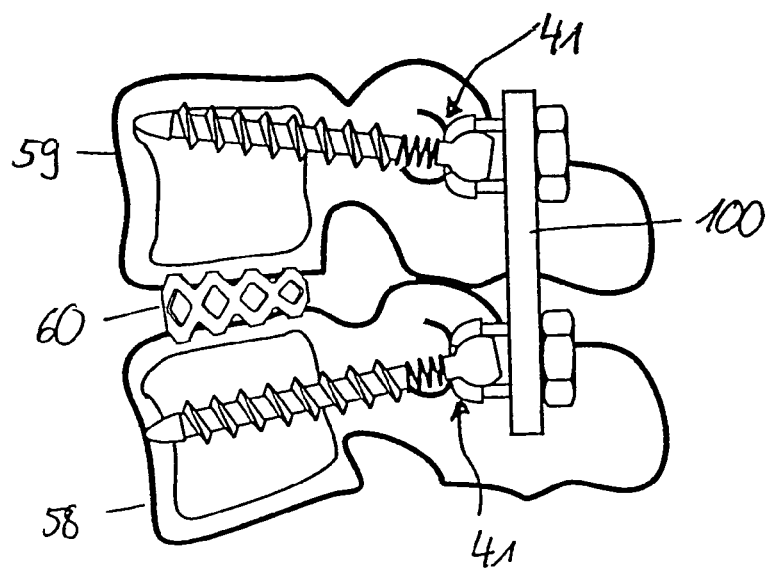
FIG. 5 shows a schematic view of a stabilization device according to another embodiment of the present invention, in which the bone anchoring element according

FIG. 5 shows an example of an application of the stabilization device for the stabilization of two vertebrae 58, 59 connected to each other by means of a fusion element 60, which replaces an intervertebral disc that has been removed. The operation corresponds to the description above.

The limited mobility of vertebrae 58, 59 relative to each other can lead to an increase in the cyclic partial load which can stimulate the growth of bone and accelerate ossification.

Figure 6A:
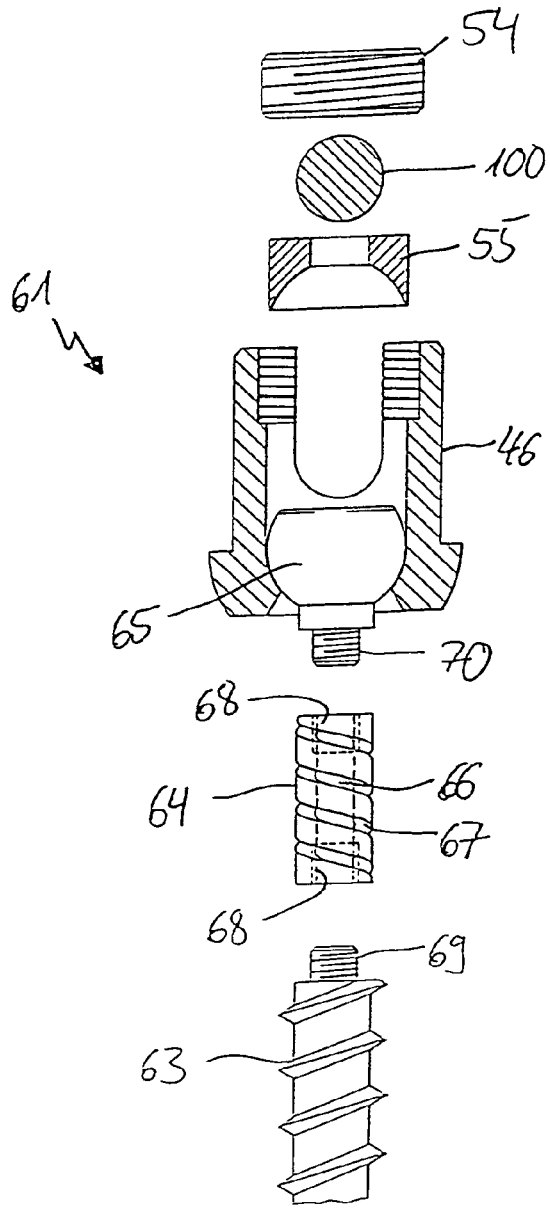
FIG. 6a shows an exploded partial view in elevation, partly in section, of another alternative embodiment of a bone anchoring element in accord with the present invention.

A further embodiment of a bone anchoring element useful in the present invention is shown in FIG. 6a. Bone anchoring element 61 differs from the bone anchoring element shown in FIG. 4 by the structure of the screw element which includes detachable components, whereas all of the other parts are identical to those in FIG. 4.

In the bone anchoring element 61, the bone screw thread section 63, the flexible section 64 and the head 65 are implemented as separate parts. Flexible section 64 consists of a cylindrical tube with a continuous coaxial bore 66 and recess 67 in its wall, which extends axially in the form of a helix in the cylinder wall and extends radially into bore 66. This arrangement forms a helical spring-like structure similar to the preceding embodiments. Adjacent to its corresponding free ends, flexible section 64 comprises, on both ends, an internal thread 68 of pre-determined length. On its end opposite to the tip to be screwed in, the bone screw thread section 63 comprises a cylindrical protrusion 69 having an outer thread that engages the inner thread 68 of flexible section 64. On its side opposite to the flattened end, head 65 also comprises a cylindrical protrusion 70 with an outer thread which engages the inner thread 68 of the flexible section 64.

In operation, the screw element of bone anchoring element 61 is assembled first by screwing together the bone anchoring section 63, the flexible section 64 and the head 65 followed by insertion of this assembly into the receiving part 46. The further operation is identical to that of the preceding embodiment.

The bone anchoring element according to this embodiment is advantageous in that it is simpler to manufacture. It has the added advantage that flexible sections 64 of varying length and stiffness can be provided and selected prior to use to suit the application at hand, and assembled with heads of a pre-determined size and thread shafts of a pre-determined length to form a screw element.

Figure 6B:
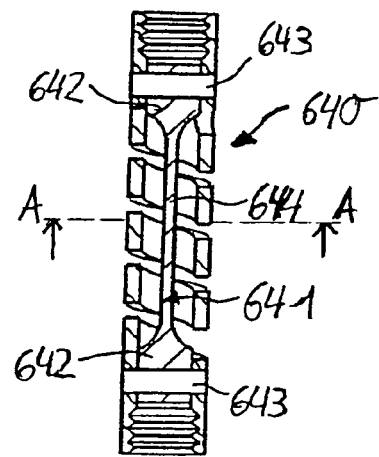
FIG. 6b shows an enlarged sectional view of a part of the bone nachoring element of FIG. 6a with a modification.

FIG. 6b shows a further development of the flexible element 64 of FIG. 6a. The flexible section 640 shown in FIG. 6b comprises a core 641 inside. The core 641 has cylindrically shaped ends 642 with a diameter such that the core can be pushed into the bore hole of the flexible section 640. The cylindrically shaped sections 642 and the flexible section 640 comprise transverse bores into which pins 643 for fixation of the core are inserted. Between the cylindrical sections 642 the core comprises a section 644 having a substantially rectangular cross section, as can be seen from FIG. 6c. The cross section of section 644 is not limited to a rectangular shape but can have another shape, for example an oval or an asymmetric shape. The core allows for adjustment of the flexural and/or torsional stiffness of the flexible section. In addition, the flexural stiffness in a particular direction depends on the orientation of the core in the bore. Preferably, the core is made from a material having a lower stiffness that the flexible element.

The polyaxial screw is not limited to the embodiment described above, but rather can be any other polyaxial screw with a three-piece screw element according to the description above. Accordingly, the first bore hole of the embodiment shown in FIG. 6a can have a smaller diameter than the screw shaft, if, in operation, the screw head, with its cylindrical projection leading, is introduced through second bore hole into receiving part first, before the flexible element and screw shaft are screwed onto screw head. In this case, it is sufficient for the first bore hole to have a diameter large enough to accommodate the cylindrical projection of the screw head to provide engagement with the flexible section.

The receiving part also can be provided such that the screw element can be inserted from below and is clamped in the receiving part by means of a pressure element, for example a snap ring. In this case, the bore hole is larger than the diameter of screw head.

Also, the rod fixation is not limited to the internal screw shown in FIG. 6a, but an additional external nut can be provided or any known type of rod fixation can be used. Alternative methods for fixation are well known to those skilled in the art and can be used in place of the fixation methods shown herein.

If the flexible element projects beyond the surface of the bone at least in part, the flexible element is capable of absorbing bending forces as well as tension and pressure forces. When the flexible element is positioned such that it does not project beyond the surface of the bone, the screw element, due to the recess of the flexible section, still is capable of giving way in response to a movement of the bone or vertebra. This prevents the development of unfavorable tension.

Figures 7A, 7B:
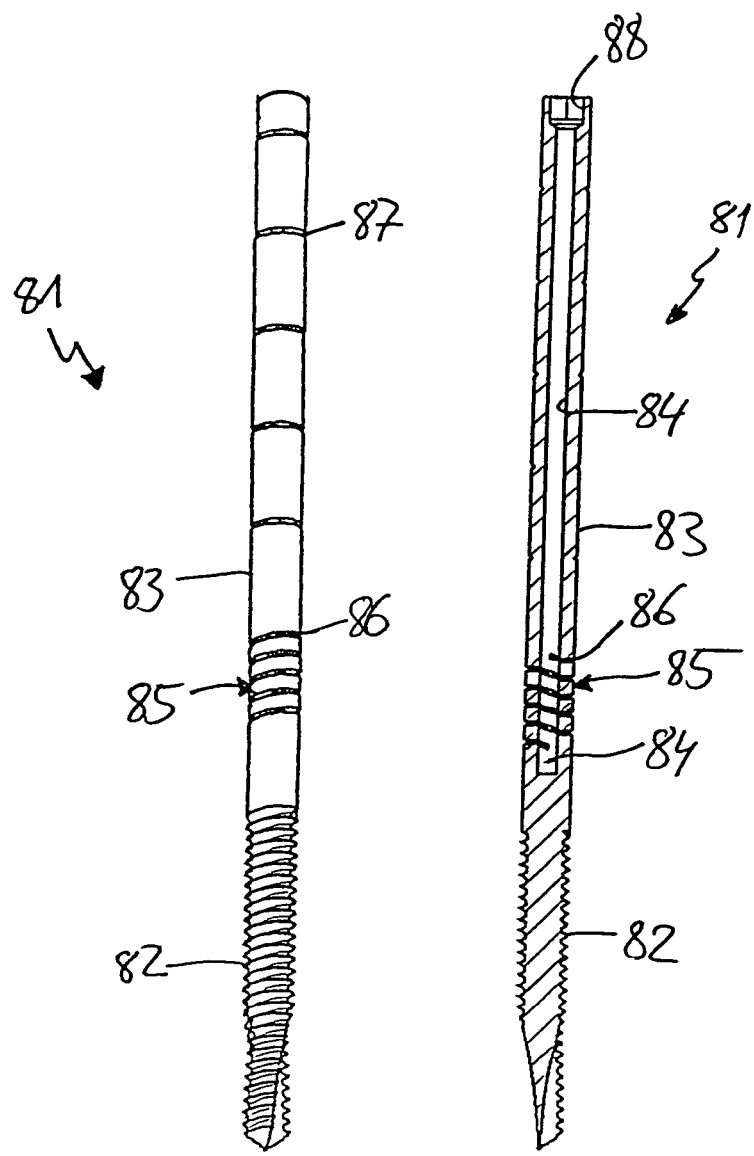

In a further embodiment shown in FIGS. 7a and 7b the bone anchoring element is implemented in the form of a Schanz screw 81. Schanz screw 81 comprises a first threaded section 82 and an adjacent cylindrical thread-free shaft section 83 with no head. A coaxial pocket bore 84 extends from the free end through to the threaded section. A recess 86 extends in the form of a helix along cylindrical wall in the direction of the screw axis over a pre-determined length and extends radially into the bore 84. Thus, the wall in a pre-determined section 85 of cylindrical section 83 is provided with said recess forming an flexible section in the form of a helical structure as in the embodiments described above. In addition, cylindrical shaft section 83 comprises notches 87 on its circumference which are arranged at a pre-determined distance from each other. In the embodiment shown, the notches are circular. Adjacent to its free end, the cylindrical shaft section comprises a hexagonal recess 88, or any other recess shape, for engaging a screw-in tool.

In operation, especially in an external stabilization device (fixator), Schanz screw 81 can be used jointly with conventional Schanz screws and conventional connecting elements and fixation rods. Schanz screw 81 is screwed into the bone fragment to be fixed such that flexible section 85 protrudes beyond the bone surface and optionally also beyond the surface of the skin. This arrangement provides for limited mobility at a predefined site depending on the stiffness of the flexible section. The Shanz screw having a flexible section also can be made in component parts similar to the bone screw as described above.

Figure 8:
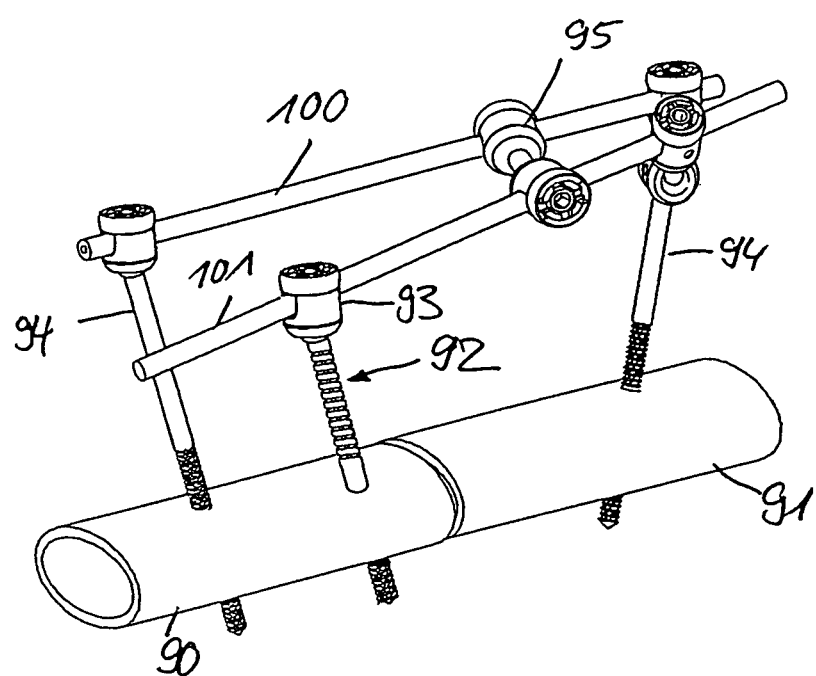
FIG. 8 shows a schematic representation of an alternative embodiment of a stabilization device in accord with the present invention.

FIG. 8 shows the application of the Schanz screw according to FIGS. 7a and 7b in an external fixator for the stabilization of bone parts 90, 91 of a fractured bone. Similar to polyaxial screw 41 above (FIG. 4), Schanz screw 92 having a flexible section also comprises for this purpose a spherical segment-shaped head (not shown herein) that is held in a receiving part 93. Bone parts 90, 91 are stabilized by means of Schanz screw 92 and conventional polyaxial bone screws 94, which are connected to rods 100, 101 and further the rods are connected together by means of a conventional connecting element 95.

Modifications of the embodiments described above are possible. In particular, elements of one embodiment may be combined with elements of another embodiment. The implementation of the screw element in the form of several parts according to the embodiment of FIG. 6a can also be used in the monoaxial bone screw according to FIGS. 3a to 3c, whereby in this case the receiving part can be screwed into the flexible section. In addition the Schanz screw according to FIGS. 7a and 7b can also be implemented in the form of several component parts. In yet another modification, the bone screw thread section and the flexible section can be connected into one part and only the head and/or the receiving part can be screwed in.

The shaft of the bone anchoring element can also have a hook shaped section instead of a bone thread for anchoring in the bone.

In yet another embodiment a separate cylindrical core is provided which is to be inserted into the bore that extends through the flexible section. This allows for additional adjustment of the stiffness of the flexible section. In another embodiment, the diameter of the flexible section differs from that of the bone screw thread section. A larger diameter can thus be used to attain increased stiffness.

Figures 9A, 9B:
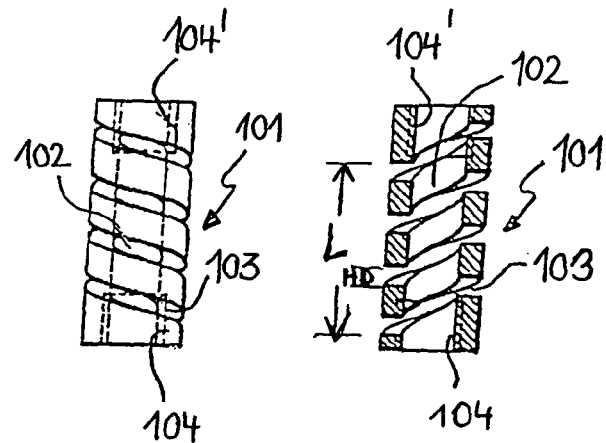

FIGS. 9a and 9b further illustrate an embodiment of a flexible section or flexible element 101 as a separate component, as discussed above. The flexible element 101 consists of a cylindrical tube with a continuous coaxial bore hole 102 and a recess 103 extending in the wall for a predefined length in the form of a helix with a predefined pitch along the direction of the cylinder axis, and which extends radially from the outer cylindrical surface into coaxial bore 102. Thereby, a helical spring-like structure is formed. The length of the helix-shaped recess in the direction of the cylinder axis, the axial height of the recess, the pitch of the helix, and the diameter of the coaxial bore hole are selected to provide a desired stiffness of the flexible element with respect to axial forces, bending forces, and torsional forces acting on the element. Adjacent to each of its free ends, flexible element 101 comprises an internal thread 104, 104' that extends axial for a predetermined length. The external diameter of the flexible element is selected according to the particular application. The selection of the afore mentioned parameters are well known to those ordinary skilled in the art.

Figure 10A:
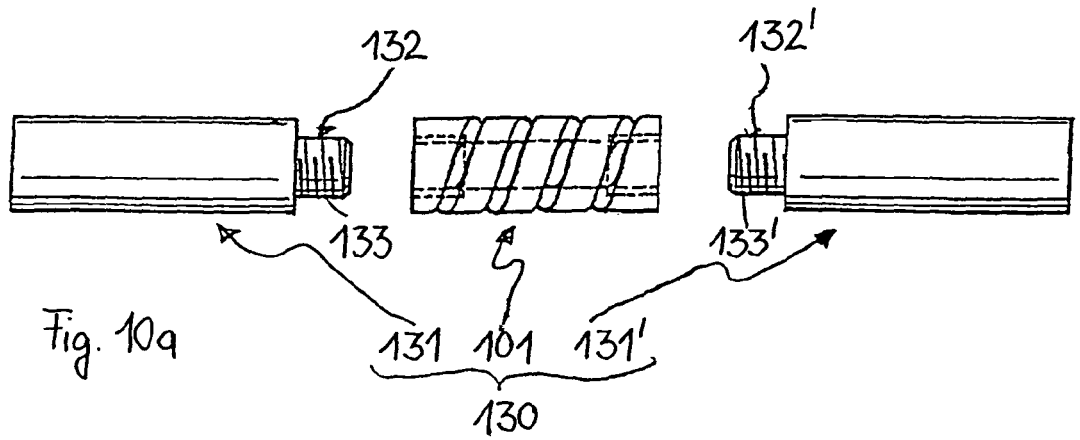
FIG. 10a shows an application the separate flexible element of FIG. 9a joining two rod-shaped elements.

As shown in FIG. 10a, flexible element 101 can be inserted as a part of a flexible rod-shaped element 130. The flexible rod-shaped element 130 consists of flexible element 101 and two cylindrical rod sections 131, 131' each comprising at their end a cylindrical projection 132, 132' with an external thread 133, 133' that cooperates with internal thread 104, 104' of flexible element 101. In this application, the rod sections and the flexible element have essentially identical external diameters. The length of rod sections 131, 131' and of flexible element 101 can be selected independently of each other with respect to a desired application. For example, the rod-shaped element can be used to connect pedicle screws at the spinal column. Owing to the properties of flexible element 101, the rod-shaped element 130 thus formed absorbs compression, extension, bending and torsional forces to a predetermined degree.

Figure 10B:
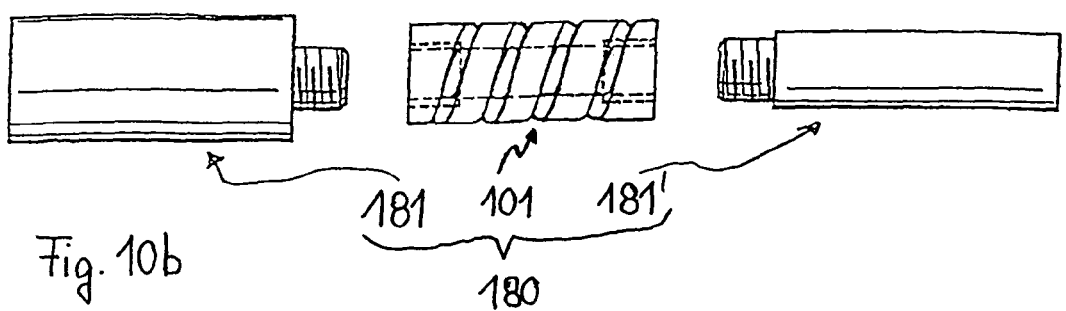

FIG. 10*b* shows an flexible rod-shaped element 180 that differs from flexible rod-shaped element 130 in that a first rigid rod section 181 has a larger external diameter than flexible element 101, and the second rigid rod section 181' has a smaller external diameter than flexible element 101. Alternatively, both rod sections can have a larger or smaller diameter than the flexible element.

Figure 11:
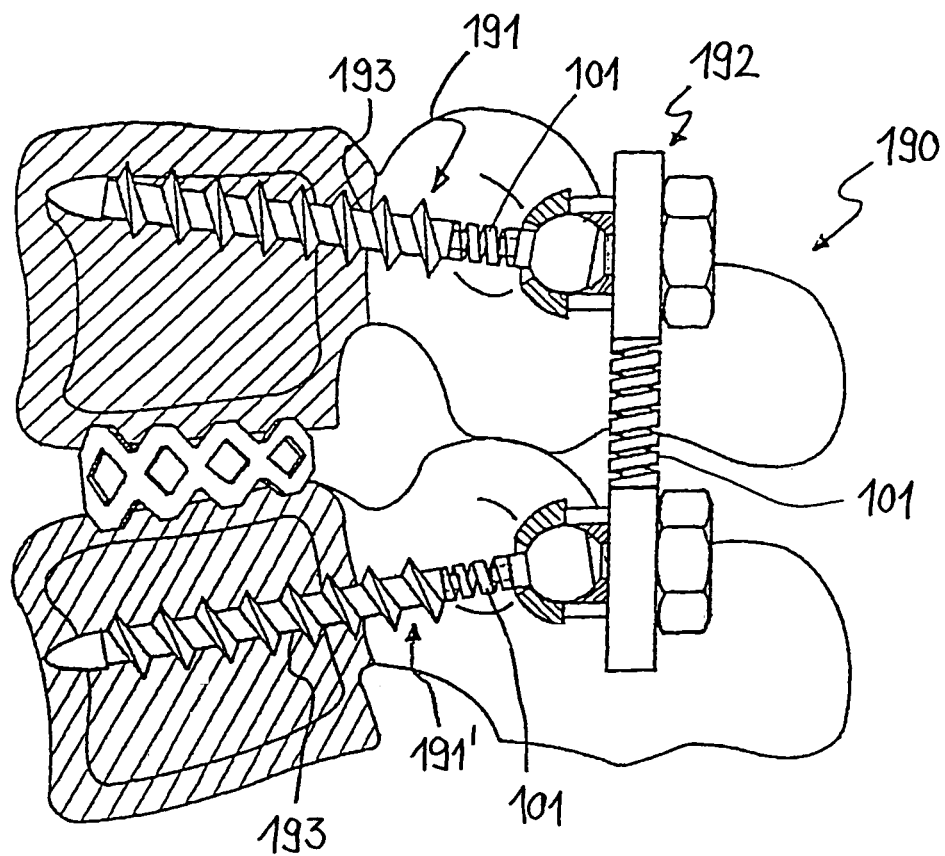
FIG. 11 shows another embodiment of a stabilization device in accord with the present invention, consisting of two three-piece bone anchoring elements and one rod-shaped element, each comprising a flexible element.

FIG. 11 shows a stabilization device 190 for the spinal column, wherein two bone anchoring elements 191, 191' with screw elements 193, each provided with a flexible element 101 according to the invention, and a flexible rod-shaped element 192 (with a flexible element 101) for connecting the two bone anchoring elements are used. The multiple-piece design of the flexible rod-shaped element and the screw element permits stabilization devices 190 to exhibit a wide variety of features by combining only a few basic elements. The stabilization device does not necessarily have to comprise bone anchoring elements with a flexible element and a flexible rod-shaped element. Depending on the field of application, it also is possible to provide only a flexible rod-shaped element and bone anchoring elements with rigid screw elements.

Figure 12:
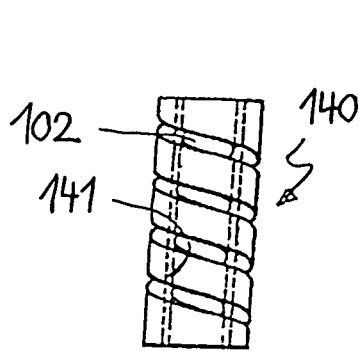
FIG. 12 shows a lateral view of another embodiment of a flexible section as a separate element in accord with certain aspects the present invention.

FIG. 12 shows another embodiment of a flexible element 140. Flexible element 140 differs from flexible element 101 only in that an internal thread 141 that extends along the entire length of the flexible element instead of the two internal threads 104, 104'.

Figure 13:
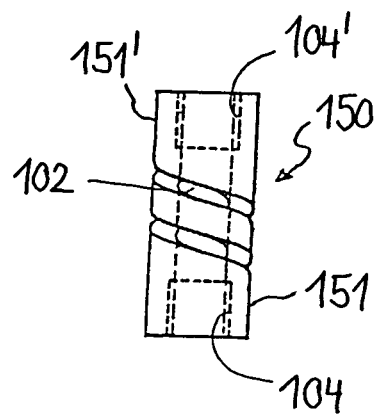
FIG. 13 shows a lateral view of a further alternative embodiment of a flexible section as a separate element in accord with certain aspects the present invention.

FIG. 13 shows an alternative embodiment of a flexible element 150. In contrast to the previously described embodiments, it comprises rigid end sections 151 and 151' and a reduced number of helical recess turns. This permits one to design the flexibility of the element independent of the length of the element.

Figures 14A, 14B:
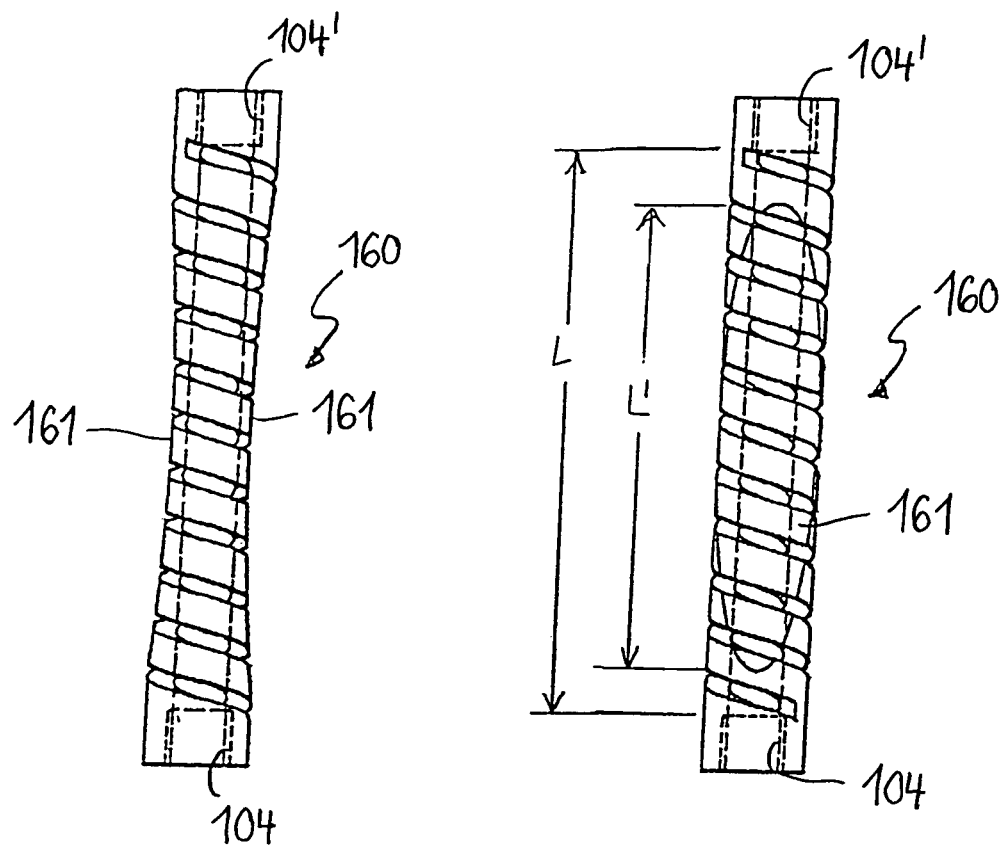

FIGS. 14*a* and 14*b* show a flexible element 160 according to another alternative embodiment which, in contrast to the preceding embodiments, comprises two regions 161 on the outer surface of the element that are offset by 180 degrees relative to each other and are concave in shape towards the center axis. The length L' of regions 161 in the axial direction is no more than equal to the length L of the helical recess, and the radius of curvature of the shaped regions 161 is such that the turns of the helical recess are not interrupted. Owing to this design, the flexible element has a "waisted shape" (i.e., a shape like a waist of a person) in a direction that is perpendicular to the center axis, thus possessing less stiffness in this direction. This permits the flexible element to have oriented stiffness which suits the purpose of certain applications.

Figure 6C:
FIG. 6c shows a sectional view of the part according to FIG. 6b along line A-A in FIG. 6b.
Figure 15:
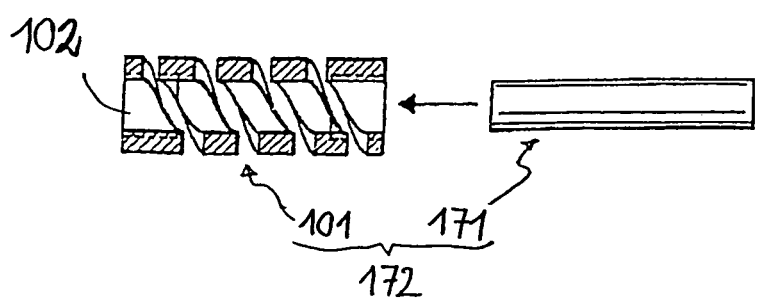
FIG. 15 shows a sectional exploded view of another alternative embodiment of a flexible section as a separate element in accord with certain aspects the present invention.

FIG. 15 shows a flexible element 172 according to a further alternative embodiment that comprises a rod-shaped core 171 that is slid into the hole in addition to the flexible element 101 described above. On the one hand, the core can serve as a limit stop in case flexible element 172 is subjected to pressure forces. On the other hand, core 171 can be used to increase the stiffness of flexible element 172 with respect to bending forces. The core can have a circular cross section or as shown in FIG. 6*c* a cross section which produces an oriented flexibility in a specific direction. The material used for the core can be the same as or a different material from that used for the flexible element. In any case the materials used for the core must be biocompatible materials, as is well known to those skilled in the art.

Figure 16:
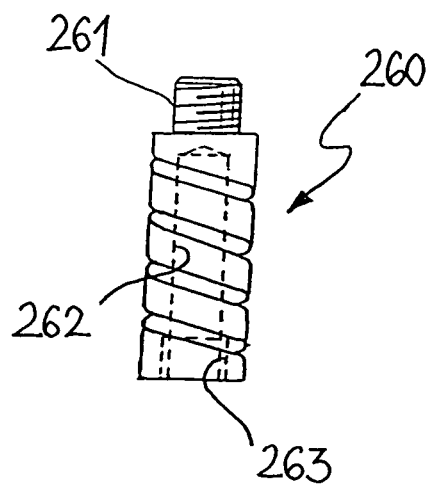
FIG. 16 shows yet a further alternative embodiment of a flexible section as a separate element in accord with certain aspects the present invention.

A flexible element 260 according to another embodiment is shown in FIG. 16. It comprises on its one end a cylindrical projection 261 with an external thread instead of a bore hole with an internal thread as described previously. Accordingly, the element to be connected to this end of the flexible element is provided with a bore hole with a corresponding internal thread. The other end of the flexible element 260 is provided with a pocket bore hole 262 in which an internal thread 263 is provided, like in the embodiments described above.

Figure 17:
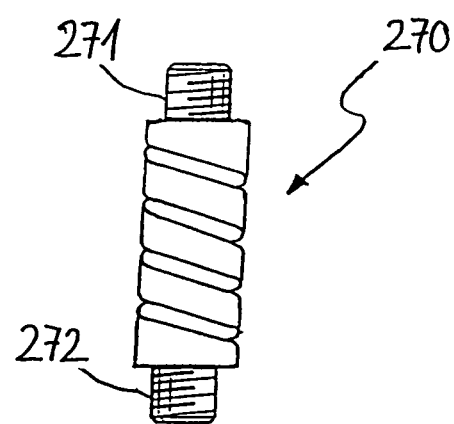
FIG. 17 shows another alternative embodiment of a flexible section as a separate element in accord with certain aspects the present invention.
Figure 18:
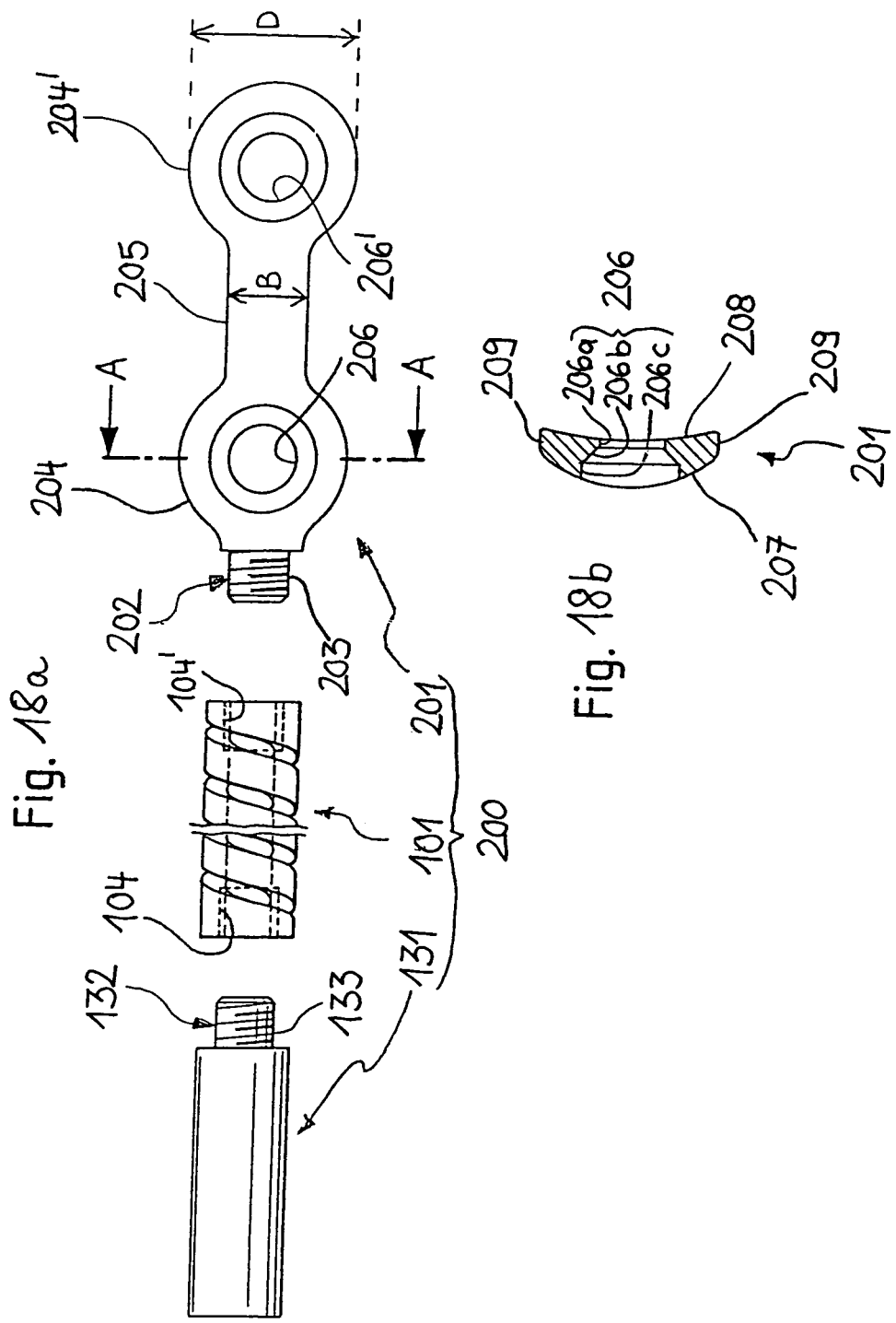
FIG. 18a shows an exploded view of a joining element consisting of a rod-shaped element, a flexible element, and a plate in accord with a further embodiment in accord with the invention.
FIG. 18b shows a sectional view of the plate of FIG. 18a along the line, A-A.

Flexible element 270 according to further alternative embodiment is shown in FIG. 17. It comprises on each of its ends a cylindrical projection 271, 272 with an external thread.

In a modification to embodiments of the flexible element described previously, another alternative embodiment comprises a flexible element that does not have a continuous bore hole from one end of the helical recess to the opposite end. Further, optionally, the recess does not extend from the outer surface of the cylinder to the bore hole throughout the axial length of the helical recess.

As a further example of an application of flexible element 101, FIG. 18*a* shows an exploded view of a connection element 200 that consists of a rod-shaped element 131, a flexible element 101 and a plate 201. Rod-shaped element 131 comprises a projection 132, shown as a cylindrical projection, with an external thread 133 for screwing into the internal thread 104 that is adjacent to the one end of flexible element 101. Plate 201 also comprises a cylindrical projection 202 with an external thread 203 for screwing into the internal thread 104' that is adjacent to the other end of flexible element 101. The plate 201 consists of two sections 204, 204' that are circular in the plan view and connected to each other by means of fin 205. The width B of fin 205 is smaller than the outer diameter D of circular sections 204, 204'. Two bore holes 206, 206' coaxial to the circular sections are provided through the plate to accommodate countersunk screw heads. As shown in FIG. 18*b*, a first side 207 of the plate preferably has a concave curvature, whereas a second side 208 of the plate preferably has a convex curvature for abutment of this side against a bone surface. The different radii of curvature of the two sides 207, 208 of plate 201 cause plate 201 to taper towards its lateral edges 209. This allows the plate to be both compact and stable As shown in FIG. 18*b*, bore holes 206, 206' comprise, adjacent to the second side 208 an orifice 206*a* and, adjacent to the orifice, a first section 206*b*, shown as a cone shaped section, and a second section 206*c* that is adjacent to the first section and first side 207. Their shape makes these bore holes 206, 206' suitable for receiving countersunk screw heads. The shape of bore holes 206, 206' also can be different from the shape described above as long as they are suitable to receive a countersunk screw head.

Figure 19:
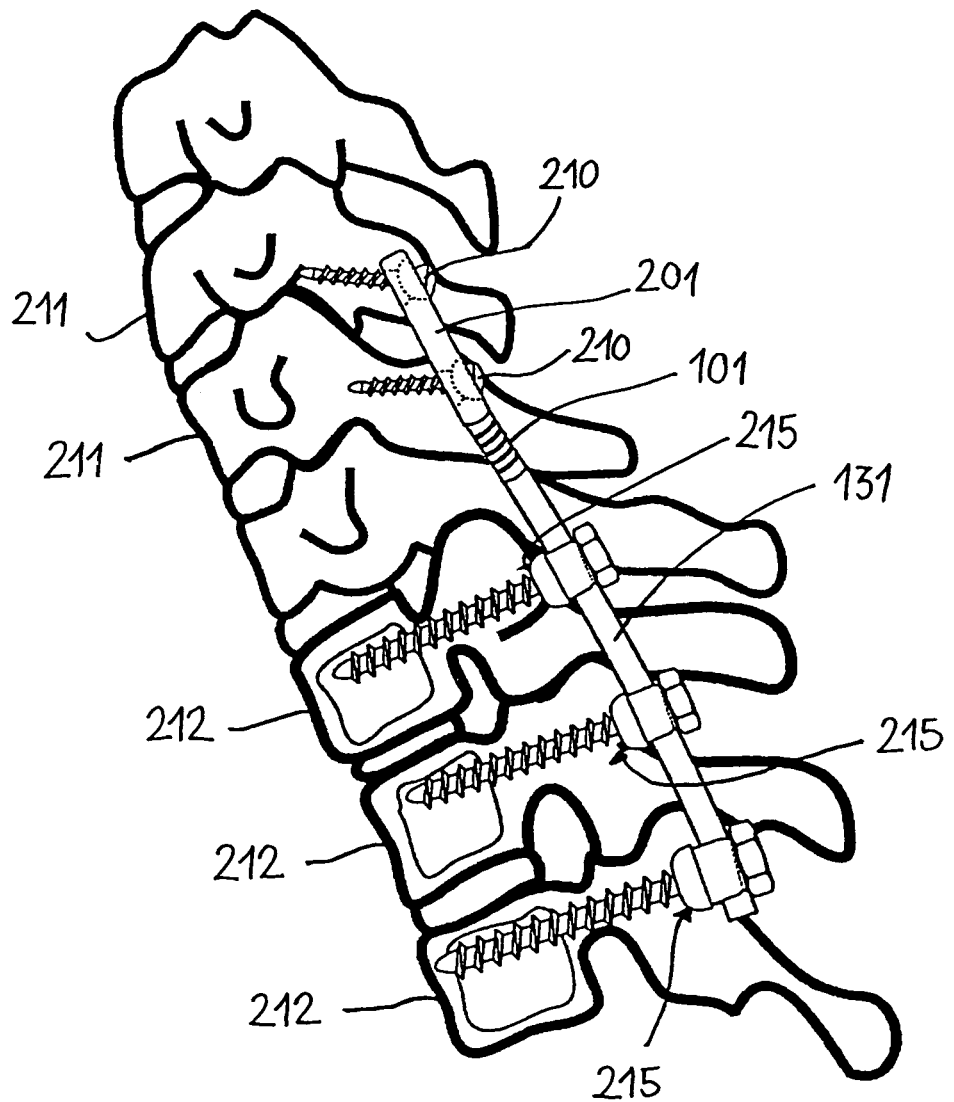
FIG. 19 is a schematic illustration showing an application a stabilization device comprising a plate of FIGS. 18a and 18b, in which the plate and a rod-shaped element connected to the plate by means of a flexible section are each anchored in vertebrae by means of bone anchoring elements.

FIG. 19 shows an example of an application using the connection element 200 of FIG. 18*a*, in which plate 201 is fixed from the posterior side to two vertebrae 211 of the cervical spine by means of two bone screws 210 and in which the rod-shaped element 131 that is connected to the plate by means of a spring-like element 101 is anchored in vertebrae 212 of the thoracic spine by means of three bone anchoring elements 215. Optionally, one or more of the bone anchoring elements comprises a flexible section.

Figure 20A:
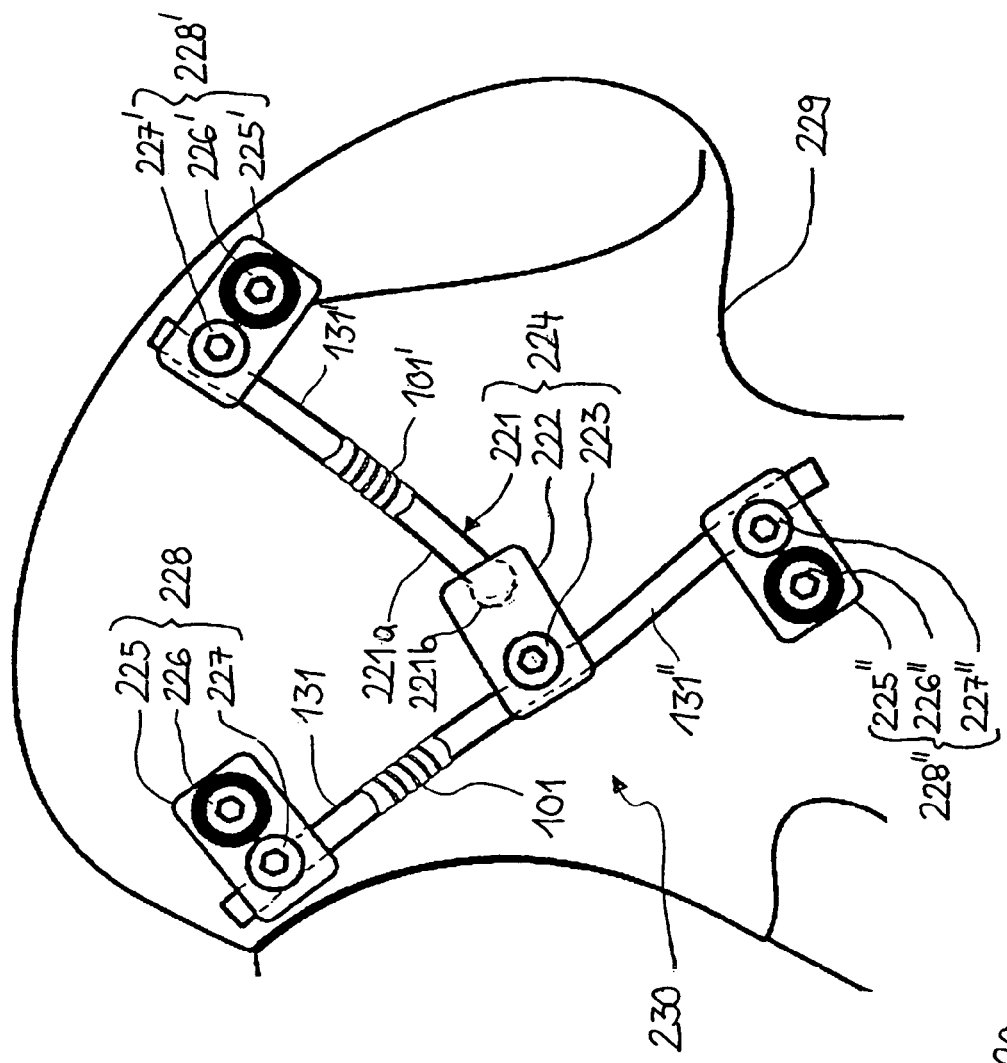
FIG. 20a shows a schematic application of a bone stabilization device comprising a flexible section according to the invention in a dynamic stabilization device for a pelvic bone.

A further example of an application of a stabilization device in accord with the present invention is illustrated in FIG. 20a. There, flexible element 101 is used in a dynamic pelvis stabilization device 230. The dynamic pelvis stabilization device consists of bone anchoring elements 228, 228', 228" that are connected to each other by means of rod-shaped elements 131, 131', 131" and flexible elements 101, 101'.

Figure 20B:
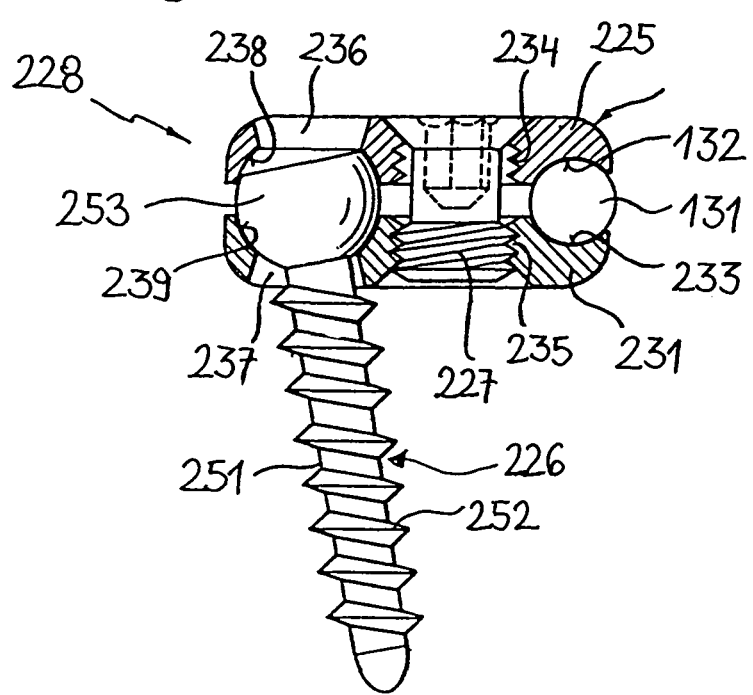

Like the two other bone anchoring elements 228', 228" the bone anchoring element 228 consists of two components 225, 231 that are screwed to each other by means of a screw 227 engaging a thread 234 in the first component 225 and a thread 235 in the second component 231 (see FIG. 20b). The top view shown in FIG. 20a shows only the top part 225. Rod-shaped element 131 is clamped between the two components 225, 231 in a recess 232 in the first part 225 and in a recess 233 in the second part 231 such that bone anchoring element 228 is firmly connected to rod-shaped element 131. Moreover, both parts 225, 231 are each provided with a bore holes 236, 237, which are in coaxial alignment in the assembled state. Adjacent to bore hole 236, a spherical recess 238 and adjacent to bore hole 237, a spherical recess 239 is provided which serve to receive the head 253 of a bone screw 226. Bone screw 226 comprises a shaft-shaped section 251 with an external bone thread 252 for screwing into the bone, and a spherical segment-shaped head section 253 with a radius that is essentially identical to the radius of spherical recesses 238, 239. Optionally, the bone screw comprises a flexible section as described and discussed above.

Like the bone anchoring element, connection element 224 consists of two parts 222, of which only one is depicted in the top view shown in FIG. 20a. Guided within a recess in the connection element, rod-shaped element 131 is clamped between these two parts 122 such that connection element 224 is firmly connected to rod-shaped element 131.

Rod element 221 consists of a head section 221b and a shaft section 221a. Head section 221b is clamped between the two parts 122 in a recess (not shown) and, thus, is connected to the two parts 222 such that it can be fixed in a certain pivot position. The head section can be ball-shaped or can have another shape which allows pivoting in the recess. At its end opposite to head section 221b, shaft section 221a comprises a cylindrical projection (not shown) with an external thread that is screwed into the internal thread (not shown) of flexible element 101'.

Figure 21:
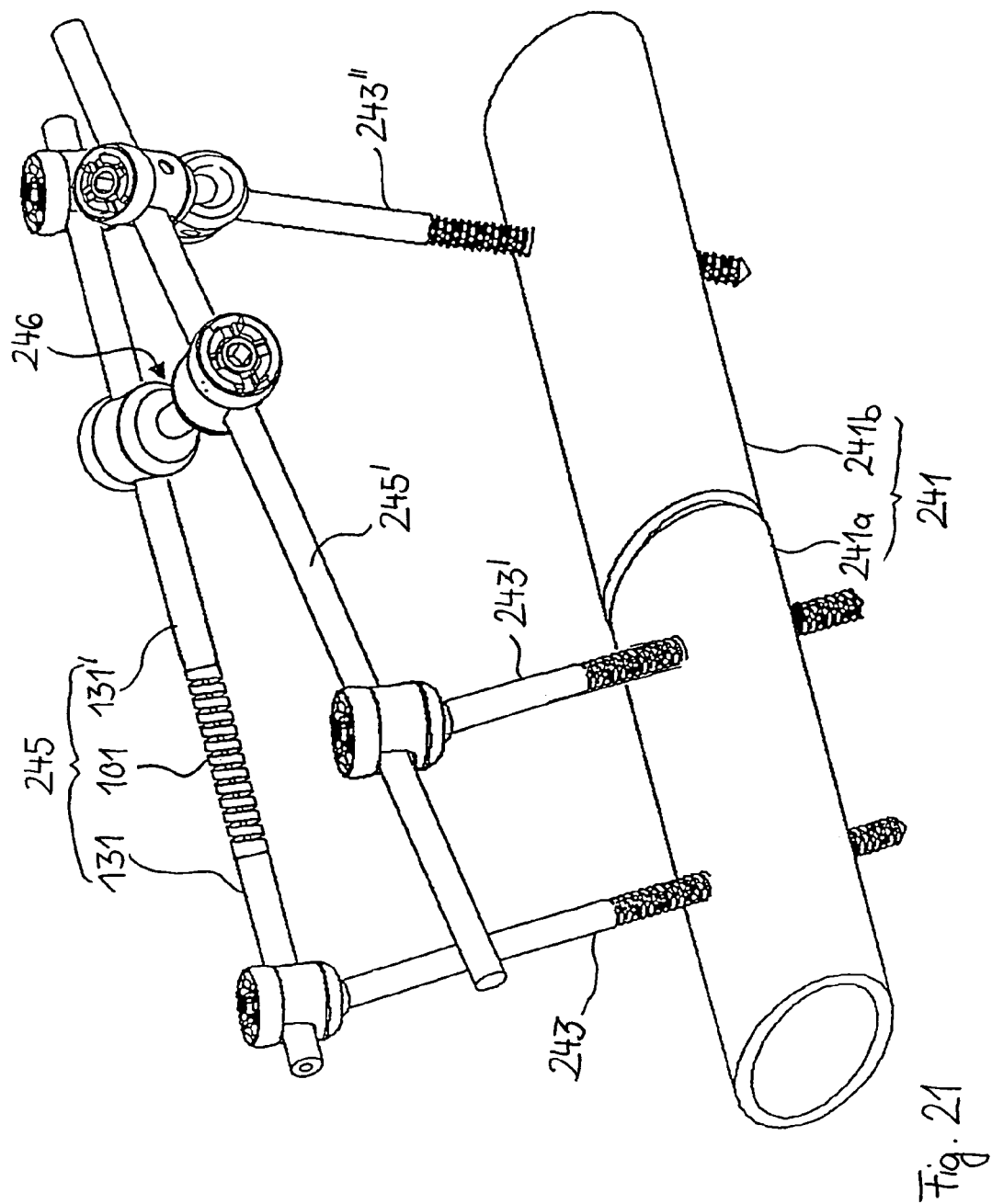
FIG. 21 shows a schematic application in an external stabilization device (fixator) with Schanz screws, which are connected to each other by means of rod-shaped elements.

A further example of an application of a stabilization device comprising a flexible element 101 according to the invention is shown in FIG. 21. In this embodiment, flexible element 101 is part of an external fixator for stabilizing a bone 241 that consists of two parts 241a and 241b.

A first and a second Schanz screw 243, 243' are screwed into first part 241a of bone 241, and a third Schanz screw 243" is screwed into the second part 241b of bone 241. The first Schanz screw 243 and the second Schanz screw 243' are connected to the third Schanz screw 243" by means of a first rod 245a second rod 245' in a generally known fashion. In addition, the first and the second rod 245, 245' are connected to each other by means of a coupling element 246 in a generally known fashion. As shown in this embodiment, the first and the second rod are firmly connected.

The first rod 245 is provided in three pieces, two rod-shaped elements 131, 131' and one flexible element 101, as described above with reference to FIG. 10a. The first rod-shaped element is firmly connected to the one end of flexible element 101 by means of a screw connection, and the second rod-shaped element is firmly connected to the other end of flexible element 101 by means of a screw connection, as described above.

The dynamic stabilization of bone 241 allows for minor motions of the two bone parts 241a and 241b relative to each other. These minor motions lead to a desirable stimulation for the fusion of the two bone parts 241a, 241b.

Depending on the field of application, one or more of the Schanz screws of the external fixator can comprise a flexible element as part of its shaft, as described above.

The manufacture of a flexible element 101 such as shown in the embodiment of FIGS. 9a and 9b by means of milling can start with a cylinder made of a biocompatible material, e.g. titanium, with a predetermined external diameter, in which a recess 103 (or slot) is milled with a thin disk milling cutter along a helix whose main axis is collinear to the main axis of the cylinder. Subsequently, preferably, a bore hole 102 can be formed along the main axis of the cylinder over the entire length of the cylinder such that helix-shaped recess 103 extends radially into bore hole 102. For the stability of flexible element 101, the runout of the helix at the transition between the helical section and the end-side section of the flexible element can be of major significance. It is therefore preferred to finish the runout of the helix at both ends of the helix with a end-milling cutter such that the sharp edge on the inside of the bore hole is removed. For this purpose, the runout is milled with a end-milling cutter at an angle tangential to the contour of the helix. Subsequently, the component is deburred on its inside and outside. Finally, an internal thread 104, 104' is formed in each of the two end sections of bore hole 102. Alternatively, the internal thread is formed continuously thoughout the entire length of the cylinder.

Figure 22:
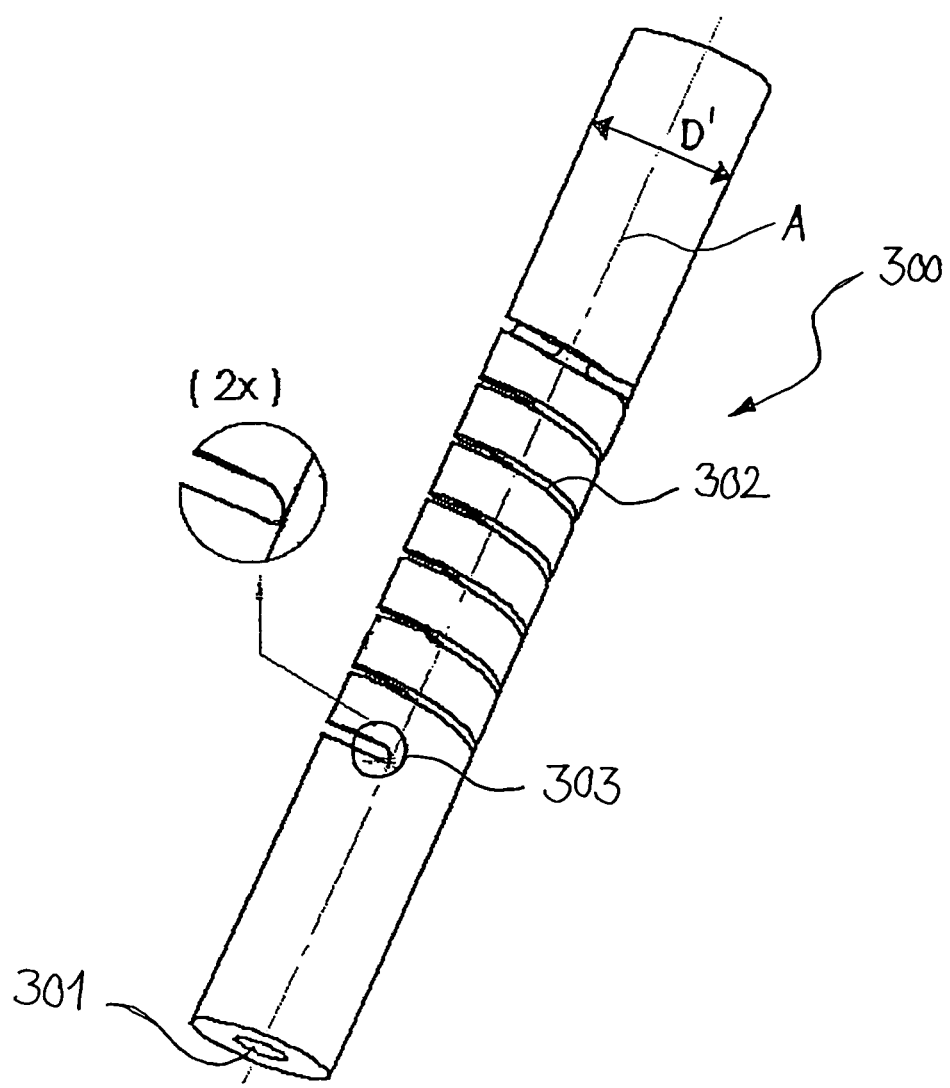
FIG. 22 shows prospective view of a flexible section in accord with the present invention manufactured by means of wire-cut electrical discharge machining (wire-cut EDM), laser treatment or water jet treatment and having runouts in the form of a quarter circle.

As an alternative to milling, a flexible element 300 can be manufactured from the cylindrical body by wire-cut-EDM, laser treatment or water jet treatment. As is shown in FIG. 22, this method also starts with a cylinder with a predetermined external diameter D', in which is formed a bore hole 301 along the main axis A over the entire length of the cylindrical body. Then, a cut is made in the wall of the hollow cylinder, thus formed, along a helix 302 using one of the procedures mentioned above depending on the thickness of the wall. The runout 303 of helix 302 is formed preferably to take the shape of a quarter circle such that the finishing of runout 303 in an additional work step as compared to the milling procedure can be dispensed with. The shape of the runout does not necessarily have to be a quarter circle but, rather, can be any other shape, such as the shape of another section of a circle by which the load peaks in the material can be kept low during operation. Moreover, it is not necessary to debur in this manufacturing procedure. Finally, an internal thread is formed at least in each of the two end sections of bore hole 301 like in the manufacturing procedure using milling.

In a modification, the procedures described above are modified by replacing the internal thread with a cylindrical projection having an external thread by turning on a lathe at a suitable point in the procedure, preferably at the start. In this case, the diameter of the bore hole must be smaller than the diameter of the cylindrical projection.

In a further modification of the manufacturing procedure, the flexible element is manufactured without a continuous bore hole.

The present invention is by no means limited to the examples of the monoaxial and polyaxial bone screws and the Shanz screw actually described herein. Other implementations of these, in particular as it concerns the receiving parts and fixation devices, are also considered in the invention. However, the shaft should have an elastic or flexible section. Moreover, the present invention can also be applied to hooks.

In another embodiment the elastic section is provided with a cover preventing the in-growth of tissue material or vessels.

The cover can be hose-shaped. Also, a polymeric cover can be used. The cover can include drugs to prevent in-growth of tissue material or vessels.

The materials which can be used for the stabilization device as a whole, for example for the screw or the rod, for the spring like element and/or for the core are biocompatible materials, for example biocompatible metals such as titanium, or biocompatible plastic materials. Also, shape memory alloys having known superelastic properties, such as nitinol, for example, can be used either for the whole screw or rod with the the flexible section or for the flexible section or the spring like element alone. If a core is provided, the core individually or in combination with the other components can also be made from a shape memory alloy.

All embodiments described above agree in that they provide the advantage of the limited mobility of the bone parts and/or vertebrae leading to an increase in the cyclical partial load which stimulates the growth of bone.

The bone stabilization device according to the invention has the further advantage that forces acting via the connecting element on the bone anchoring elements when the bone parts or vertebrae are in motion are decoupled totally or partially from the part of the bone anchoring element which is firmly anchored in the bone. Therefore, loosening of the bone anchoring element can be avoided. This is particularly relevant for the stabilization of vertebrae where a limited motion of the vertebrae with respect to each other could be desired.

The embodiments described above and shown herein are illustrative and not restrictive. The scope of the invention is indicated by the claims rather than by the foregoing description and attached drawings. The invention may be embodied in other specific forms without departing from the spirit of the invention. Accordingly, these and other changes which come within the scope of the claims are intended to be embraced therein.

What is claimed is:

1. A bone stabilization device comprising:
    a plurality of bone anchoring elements; and
    a connecting element connecting at least two of the bone anchoring elements, wherein at least one of the bone anchoring elements comprises:
        a screw element having a shaft having a threaded portion and a flexible section as separate detachable components, the threaded portion comprising a bone thread having a root and a crest for anchoring into bone tissue and the flexible section having an essentially cylindrical body with an outer surface, a bore, and a helical slotted opening in the outer surface of the cylindrical body, the helical slotted opening extending radially inward to the bore, the screw element further having a head adjacent to the flexible section, the diameter of the bore of the flexible section being less than a diameter at the root of the bone thread; and
        a receiving part defining a bore for receiving the head, the receiving part further comprising a U-shaped recess for inserting the connecting element, wherein the receiving part and the shaft are pivotably connected.

2. The bone stabilization device according to claim 1, wherein the flexible section comprises a first end and a second end opposite thereto, each of the opposite ends of said body comprising a coaxial hole and at least one of these ends comprising an internal thread for connecting to the shaft and/or the head.

3. The bone stabilization device according to claim 2, wherein an internal thread is provided at each of the two ends.

4. The bone stabilization device according to claim 1, wherein the connecting element further comprises a second flexible section having a second essentially cylindrical body with a second outer surface and a second helical slotted opening in the second outer surface, the second helical slotted opening extending radially inward.

5. The bone stabilization device according to claim 1, wherein the bone anchoring device is a monoaxial, a polyaxial or a Schanz screw.

6. The bone stabilization device according to claim 1, wherein a first end of said body further comprises a first cylindrical projection with a first external thread for connecting to the shaft or to the head.

7. The bone stabilization device according to claim 6, wherein a second end of said body further comprises a coaxial bore hole adjacent to its second end.

8. The bone stabilization device according to claim 7, further comprising an internal thread in at least a section of the coaxial bore hole that is adjacent to the second end.

9. The flexible element according to claim 1, comprised of a body-compatible material.

10. The flexible element according to claim 1, comprised of titanium.

11. The bone stabilization device according to claim 1, wherein the connecting element further comprises a rod-shaped element for connecting two bone anchoring elements, the rod-shaped element comprising a first rigid rod section and a flexible element with first and second ends, and wherein the first rigid rod section is connected to the first end of the flexible element.

12. The bone stabilization device according to claim 11, wherein the rod-shaped element further comprises a second rigid rod section and the second rigid rod section is connected to the second end of the flexible element.

13. The bone stabilization device according to claim 1, wherein the connecting element further comprises a plate having an end and said end having (i) a cylindrical projection with an external thread or (ii) a bore hole with an internal thread, and further comprising a flexible element attached to said end.

14. A bone anchoring element comprising:
    a screw element having a shaft having a threaded portion and a flexible section as separate detachable components, the threaded portion comprising a bone thread having a root and a crest for anchoring into bone tissue and the flexible section having an essentially cylindrical body with an outer surface, a bore, and a helical slotted opening in the outer surface of the cylindrical body, the helical slotted opening extending radially inward to the bore, the screw element further having a head adjacent to the flexible section, the diameter of the bore of the flexible section being less than a diameter at the root of the bone thread; and
    a receiving part defining a bore for receiving the head, the receiving part further comprising a U-shaped recess for inserting a rod, wherein the receiving part and the shaft are pivotably connected.

15. The bone stabilization device according to claim 14, wherein the flexible section comprises a first end and a second end opposite thereto, each of the opposite ends of said body comprising a coaxial hole and at least one of these ends comprising an internal thread for connecting to the shaft and/or the head.

16. The bone stabilization device according to claim 15, wherein an internal thread is provided at each of the two ends.

17. The bone stabilization device of claim 14, where a first end of said body further comprises a first cylindrical projection with a first external thread for connecting to the shaft or to the head.

18. The bone stabilization device according to claim 17, wherein a second end of said body further comprises a coaxial bore hole adjacent to its second end.

19. The bone stabilization device according to claim 18, further comprising an internal thread in at least a section of the coaxial bore hole that is adjacent to the second end.

* * * * *

UNITED STATES PATENT AND TRADEMARK OFFICE
CERTIFICATE OF CORRECTION

| | | |
|---|---|---|
| PATENT NO. | : 8,632,570 B2 | |
| APPLICATION NO. | : 10/982188 | |
| DATED | : January 21, 2014 | |
| INVENTOR(S) | : Lutz Biedermann et al. | |

It is certified that error appears in the above-identified patent and that said Letters Patent is hereby corrected as shown below:

In the Specification

Column 2, line 34      Delete "strechable"

Insert -- stretchable --

Column 5, line 17      Delete "of the"

Column 5, line 44      Delete "a"

Insert -- an --

Column 6, line 2      Delete "nachoring"

Insert -- anchoring --

Column 6, line 17      After "application"

Insert -- of --

Column 6, line 26      After "aspects"

Insert -- of --

Column 6, line 29      After "aspects"

Insert -- of --

Column 6, line 32      After "aspects"

Insert -- of --

Signed and Sealed this
Second Day of December, 2014

Michelle K. Lee
*Deputy Director of the United States Patent and Trademark Office*

In the Specification (continued)

| | |
|---|---|
| Column 6, line 37 | After "aspects" Insert -- of -- |
| Column 6, line 40 | After "aspects" Insert -- of -- |
| Column 6, line 42 | After "aspects" Insert -- of -- |
| Column 7, line 56 | Delete "is" Insert -- it -- |
| Column 8, line 65 | Delete "an" Insert -- a -- |
| Column 9, line 28 | Delete "shead" Insert -- head -- |
| Column 9, line 57 | Delete "it side" Insert -- its side -- |
| Column 10, line 5 | Delete "an" Insert -- a -- |
| Column 11, line 17 | Delete "that" Insert -- than -- |
| Column 11, line 60 | Delete "an" Insert -- a -- |
| Column 12, line 9 | Delete "Shanz" Insert -- Schanz -- |

CERTIFICATE OF CORRECTION (continued)
U.S. Pat. No. 8,632,570 B2

In the Specification (continued)

| | |
|---|---|
| Column 13, line 15 | Delete "an" |
| | Insert -- a -- |
| Column 14, line 50 | Delete "stable" |
| | Insert -- stable. -- |
| Column 15, line 18 | Delete "a" |
| Column 16, line 24 | Delete "a" |
| | Insert -- an -- |
| Column 16, line 61 | Delete "Shanz" |
| | Insert -- Schanz -- |

In the Claims

| | |
|---|---|
| Column 17, Claim 1, line 39 | Delete "clement" |
| | Insert -- element -- |